(12) United States Patent
Gaxiola et al.

(10) Patent No.: US 8,168,864 B2
(45) Date of Patent: *May 1, 2012

(54) TRANSGENIC POLLEN EXPRESSING EXOGENOUS PLANT VACUOLAR PYROPHOSPHATASE AND METHODS FOR INCREASING SEED PRODUCTION IN PLANTS

(75) Inventors: Roberto A. Gaxiola, Mansfield Center, CT (US); Seth L. Alper, Boston, MA (US); Gerald R. Fink, Chestnut Hill, MA (US)

(73) Assignee: Beth Israel Deaconess Medical Center, Boston, MA (US)

( * ) Notice: Subject to any disclaimer, the term of this patent is extended or adjusted under 35 U.S.C. 154(b) by 294 days.

This patent is subject to a terminal disclaimer.

(21) Appl. No.: 11/135,165

(22) Filed: May 23, 2005

(65) Prior Publication Data

US 2005/0278808 A1    Dec. 15, 2005

Related U.S. Application Data

(63) Continuation of application No. 09/934,088, filed on Aug. 20, 2001, now abandoned.

(60) Provisional application No. 60/226,223, filed on Aug. 18, 2000.

(51) Int. Cl.
*A01H 5/00* (2006.01)
*C12N 15/82* (2006.01)
*C12N 5/04* (2006.01)

(52) U.S. Cl. ........ 800/295; 800/298; 800/278; 800/289; 800/290; 435/419; 435/468

(58) Field of Classification Search ........................ None
See application file for complete search history.

(56) References Cited

U.S. PATENT DOCUMENTS

| | | | |
|---|---|---|---|
| 4,707,359 A | 11/1987 | McMullen | |
| 4,945,050 A | 7/1990 | Sanford et al. | |
| 5,071,962 A | 12/1991 | Morrison | |
| 5,100,792 A | 3/1992 | Sanford et al. | |
| 5,294,593 A | 3/1994 | Khan | |
| 5,310,673 A | 5/1994 | Shibata | |
| 5,451,240 A | 9/1995 | Trowbridge | |
| 5,538,877 A | 7/1996 | Lindquist et al. | |
| 5,750,862 A | 5/1998 | John | |
| 5,837,545 A | 11/1998 | Guy et al. | |
| 5,859,338 A | 1/1999 | Meyerowitz | |
| 5,977,441 A | 11/1999 | Oliver | |
| 6,063,731 A | 5/2000 | Back | |
| 6,069,009 A | 5/2000 | Pepin | |
| 6,087,175 A | 7/2000 | John | |
| 6,087,176 A | 7/2000 | Durzan | |
| 6,198,026 B1 | 3/2001 | Fabijanski | |
| 6,200,808 B1 | 3/2001 | Simmonds | |
| 6,239,327 B1 | 5/2001 | Grossniklaus | |
| 6,248,935 B1 | 6/2001 | Cigan | |
| 6,255,564 B1 | 7/2001 | Fabijanski | |
| 6,936,750 B2 * | 8/2005 | Blumwald et al. | 800/298 |
| RE39,114 E | 5/2006 | Barry | |
| 7,041,875 B1 | 5/2006 | Blumwald | |
| 7,071,378 B1 | 7/2006 | Bonello | |
| 7,071,382 B2 | 7/2006 | Cahoon | |
| 7,534,933 B2 | 5/2009 | Gaxiola | |
| 8,003,852 B2 | 8/2011 | Gaxiola et al. | |
| 2002/0023282 A1 | 2/2002 | Gaxiola | |
| 2002/0178464 A1 | 11/2002 | Gaxiola | |
| 2003/0213015 A1 | 11/2003 | Gaxiola | |
| 2005/0262598 A1 | 11/2005 | Gaxiola | |
| 2009/0288222 A1 | 11/2009 | Gaxiola et al. | |

FOREIGN PATENT DOCUMENTS

| | | |
|---|---|---|
| WO | WO 97/26365 | 7/1997 |
| WO | WO 99/05902 | 2/1999 |
| WO | WO 99/47679 | 9/1999 |
| WO | WO 99/61616 | 12/1999 |
| WO | WO 00/75330 | 12/2000 |
| WO | WO 01/33945 | 5/2001 |
| WO | WO 01/45494 | 6/2001 |
| WO | WO 02/15674 | 2/2002 |
| WO | WO 02/16558 | 2/2002 |
| WO | WO 2007/049275 | 5/2007 |
| WO | WO 2007/053974 | 5/2007 |
| WO | WO 2009/020528 | 2/2009 |

OTHER PUBLICATIONS

Sarasian et al. (Proc. Natl. Acad. Sci., 89:1775-1779, 1992).*
Kim et al. (Plant Physiol., 106:375-382, 1994).*
Gaxiola et al. (PNAS, 96:1480-1485, Published Feb. 16, 1999).*
Kay et al. (Science, 236:1299-1302, 1987).*
Barkla et al. (Annu. Rev. Plant Physiol. Plant Mol. Biol., 47:159-184, 1996.*
Rausch et al. (J. Plant Physiol. 148:425-433, 1996).*
Tanaka et al. (Biochem Biophys. Res. Commun., 190:1110-1114; 1993).* Jens Lerchl, et al., Molecular Cloning, Characterization and Expression Analysis of Isoforms Encoding Tonoplast-Bound Proton-Translocating Inorganic Pyrophosphatase in Tobacco; *Plant Molecular Biology* 29. (1995); pp. 833-840.
Y. Kim, et al., Isolation and characterization of cDNAs Encoding the Vacular H+- Phrophosphatas of *Beta vulgaris; Plant Physiol.* (1994); pp. 375-382.
R. G. Zhen, et al., The Molecular and Biochemical Basis of Pyrophosphate-Energized Proton Translocation at the Vacuolar Membrane; *Advances in Botanical Research, The Plant Vacuole*, vol. 25, Academic Press (1997); pp. 298-337.
J. P. Gogarten, et al., The Use of Antisense mRNA to Inhibit the Tonoplast H+ ATPase in Carrot; *The Plant Cell*, vol. 4, (1992); pp. 851-864.
H. Sze, et al., Energization of Plant Cell Membranes by H+-Pumping ATPases: Regulation and Biosynthesis; *The Plant Cell*, vol. 11, (Apr. 1999); pp. 677-689.
R. A. Leigh, Solute Composition of Vacuoles, *Advances in Botanical Research, The Plant Vacuole*, vol. 25, Academic Press (1997); pp. 171-194.
R. Töpfer, et al., A Set of Plant Expression Vectors for Transcriptional and Translational Fusions; *Nucleic Acids Research*, vol. 15, No. 14 (1987); p. 5890.

(Continued)

*Primary Examiner* — Vinod Kumar
(74) *Attorney, Agent, or Firm* — Hamilton, Brook, Smith & Reynolds, P.C.

(57) ABSTRACT

Methods are provided for imparting desirable phenotypic traits to transgenic plants, among them being increased tolerance to external stresses such as drought, freezing temperatures, high salt conditions, and the like. In addition, the present invention is directed toward methods for increasing the yield of seeds from plants by using the pollen from a transgenic plant transformed to overexpress a vacuolar proton-pumping pyrophosphatase to fertilize plants, and to the pollen of transgenic plants itself.

43 Claims, 15 Drawing Sheets

OTHER PUBLICATIONS

M. E. Galway, et al., Growth and Ultrastructure of *Arabidopsis* Root Hairs: The *rhd3* Mutation Alters Vacuole Enlargement and Tip Growth; *Planta* 201 (1997); pp. 209-218.

A. S. Gupta, et al., Maintenance of Phtosynthesis at Low Leaf Water Potential in Wheat; *Plant Physiol.* 89 (1989); pp. 1358-1365.

P. A. Rea, et al., Tonoplast Adenosine Triphosphatase and Inorganic Pyrophosphatase; *Methods in Plant Biochemistry*, vol. 3, Academic Press (1997); pp. 385-405.

J. M. Davies, The Bioenergetics of Vacular H+ Pumps, *Advances in Botanical Research, The Plant Vacuole*, vol. 25, Academic Press (1997); pp. 340-363.

Q. Al-Awqati, Chloride Channels of Intracellular Organelles; *Current Opinion in Cell Biology*, (1995); pp. 504-508.

K. D. Hirschi, et al., CAX1, an $H^+/Ca^{2+}$ Antiporter From Arabidopsis, *Proc. Natl. Acad. Sci. USA* vol. 93, (1996), pp. 8782-8786.

X. S. Xie et al., Isolation and Reconstitution of the Chloride Transporter of Clathrin-coated Vesicles, *J. Biol. Chem.*, vol. 264, No. 32, Nov. 15, 1989, pp. 18870-18873.

M. A. Apse, et al., Salt Tolerance Confered by Overexpression of a Vacuolar NA+/H+ Antiport in Arabidopsis, *Science*, vol. 285, Aug. 20, 1995; pp. 1256-1258.

J. M. Davies, Vacuolar Energization: Pumps, Shunts and Stress, Journal of Experimental Botany, vol. 48, No. 308, Mar. 1997, pp. 633-641.

E. Ballesteros, et al., Na+/H+ Antiport Activity in Tonoplast Vesicles Isolated From Sunflower Roots induced by NaCl Stress, *Physiologia Plantarum*, vol. 99, (1997) pp. 328-334.

T. Rausch et al., Salt Stress Responses of Higher Plants: The Role of Proton Pumps and Na+/H+ Antiporters. *J. Plant Physiol.*, vol. 148 (1996) pp. 425-433.

R. Serrano et al., Microbial Models and Salt Stress Tolerance in Plants, *Critical Reviews in Plant Sciences*, vol. 13, No. 2, (1994), pp. 121-138.

E. J. Kim et al., Heterologous Expression oof Plant Vacuolar Pyrophosphatase in Yeast Demonstrates Sufficiency of the Substrate-Binding Subunit for Proton Transport, *Proc. Natl. Acad. Sci. USA*, vol. 91; Jun. 1994, pp. 6128-6132.

P. Hajdukiewicz et al. The Small, Versitile p*PZP* family of *Agrobacterium* Binary Vectors for Plant Transformation, *Plant Molecular Biology* 25 (1994), pp. 989-994.

J. Schiefelbein et al., Pollen Tube and Root-Hair Tip Growth is Disrupted in a Mutant of *Arabidopsis thaliana, Plant Physiol.* (1993), pp. 979-985.

K. Schumaker et al., A $Ca^{2+}/H^+$ Antiport System Driven by the Proton Electrochemical Gradient of a Tonoplast $H^+$-ATPase from Oat Roots, *Plant Physiol.* (1985), pp. 1111-1117.

R. Gaxiola et al., Drought- and Salt-Tolerant Plants Result From Overexpression of the AVP1 $H^+$-Pump, *Proc. Natl. Acad. Sci. USA.*, Sep. 25, 2001, vol. 98, No. 20, pp. 11444-11449.

V. Sarafian et al., Molecular Cloning and Sequence of cDNA Encoding the Pyrophosphate-energized Vacuolar Membrane Proton Pump of *Arabidopsis thaliana, Proc. Natl. Acad. Sci. USA*, vol. 89, Mar. 1992, pp. 1775-1779.

R. Gaxiola et al., The *Arabidopsis thaliana* Proton Transporters, AtNhx1 and Avp1, Can Function in Cation Detoxification in Yeast, *Proc. Natl. Acad. Sci. USA*, vol. 96, Feb. 1999, pp. 1480-1485.

M. Stitt, Pyrophosphate as an Energy Donor in the Cytosol of Plant Cells: an Enigmatic Alternative to ATP, *Bot. Acta 111* (1998) 167-175.

Antebi, A. and Fink, G. R., "The Yeast $Ca^{2+}$-ATPase Homologue, PMR1, is Required for Normal Golgi Function and Localizes in a Novel Golgi-Like Distribution," *Mol. Biol. Cell*, 3;633-654, (1992).

Ballester, R., et al., "Genetic Analysis of Mammalian GAP Expressed in Yeast," *Cell*, 59:681-686, (1989).

Baltscheffsky, M., et al., "$H^+$-Proton-Pumping Inorganic Pyrophosphatase: A Tightly Membrane-Bound Family," *FEBS Letters*, 452:121-127, (1999).

Barkla, B.J., et al., "The Plant Vacuolar $Na^+/H^+$ Antiport," *Symp. Soc. Exp. Biol.*, 48:141-153, (1994).

Barkla, B.J., et al., "Tonoplast $Na^+/H^+$ Antiport Activity and Its Energization by the Vacuolar $H^+$-ATPase in the Halophytic Plant Mesembryanthemum Crystallinum $L^1$," *Plant Physiol.*, 109:549-556, (1995).

Bassham, D.C. and Raikhel, N. V., "An Arabidopsis VPS45p Homolog Implicated in Protein Transport to the Vacuole," *Plant Physiol.*, 117:407-415, (1998).

Bechtold, N., et al., "In Planta Agrobacterium Mediated Gene Transfer by Infiltration of Adult Arabidopsis Plants," *C.R. Jances Acad. Sci. Ser. III Sci. Vie*, 361:1194-1199, (1993).

Becker, D., "Bynary Vectors Which Allow the Exchange of Plant Selectable Markers and Reporter Genes," *Nucleic Acids Research*, 18: pp. 203, (1990).

Bidonde, S., et al., "Expression and Characterization of Three Tomato 1-Aminocyclopropane-1-Carboxylate Oxidase cDNA in Yeast," *Eur. J. Biochem.*, 253:20-26, (1998).

Burbidge, A., et al., "Structure and Expression of a cDNA Encoding a Putative Neoxanthin Cleavage Enzyme (NCE), Isolated From a Wilt-Related Tomato (Lycopersicon Esculentum Mill.) Library," *Journal of Experimental Botany*, 47(317):2111-2112, (1997).

Carystinos, G.D., et al. "Vacuolar $H^+$-Translocating Pyrophosphatase is Induced by Anoxia or Chilling in Seedlings of Rice$^1$," *Plant Physiol.*, 108:641-649, (1995).

Counillon, L., et al., "A Point Mutation of the $Na^+/H^+$ Exchanger Gene (NHE1) and Amplification of the Mutated Allele confer Amiloride Resistance Upon Chronic Acidosis," *Proc. Natl. Acad. Sci. USA*, 90:4508-4512, (1993).

Cunningham, S.D., and Ow., D. W., "Promises and Prospects of Phytoremediation," *Plant Physiol.*, 110:715-719, (1996).

Darley, C.P., et al., "Chill-Induced Changes in the Activity and Abundance of the Vacuolar Proton-Pumping Pyrophosphatase From Mung Bean Hypocotyls," *Plant Physiol.*, 109:659-665, (1995).

Drews, G., et al., "In Situ Hybridization to RNA in Plant Tissue," *Plant Molec. Biol. Rep.*, 5:242-250, (1988).

Drozdowicz, Y.M., et al., "AVP2, a Sequence-Divergent, $K^+$-Insensitive $H^+$-Translocating Inorganic Pyrophosphatase from Arabidopsis," *Plant Physiol.*, 123:353-362, (2000).

Farré, E. M., et al., "Accceleration of Potato Tuber Sprouting by the Expression of a Bacterial Pyrophosphatase," *Nature Biotechnology*, 19: 268-272 (2001).

Gaxiola, R., et al., "A Novel and Conserved Salt-Induced Protein is an Important Determinant of Salt Tolerance in Yeast," The EMBO Journal, 11(9):3157-3164, (1992).

Gaxiola, R.A., et al., "The Yeast CLC Chloride Channel Functions in Cation Homeostasis," *Proc. Natl. Acad. Sci. USA*, 95:4046-4050, (1998).

Gibeaut, D.M., et al., "Maximal Biomass of *Arabidopsis thaliana* Using a Simple, Low-Maintenance Hydroponic Method and Favorable Environmental Conditions," *Plant Physiol.*, 115:317-319, (1997).

Gietz, D., et al., "Improved Method for High Efficiency Transformation of Intact Yeast Cells," *Nucl. Acids Res.*, 20:p. 1425, (1992).

Guiltinan, M.J. and McHenry, L., "Epitope Tagging for the Detection of Fusion Protein Expression in Transfenic Plants," *Methods Cell Biol.*, 49:143-151, (1995).

Guo, H.H., et al., "Protein Tolerance to Random Amino Acid Change," *PNAS*, 101(25):9205-9210, (2004).

Haughn, G.W. and Somerville, C., "Sulfonylurea-resistant Mutants of *Arabidopsis thaliana*," *Mol Gen Genet*, 204:430-434 (1986).

Hechenberger, M., et al., "A Family of Putative chloride Channels From *Arabidopsis* and Functional Complementation of a Yeast Strain With a CLC Gene Disruption," *The Journal of Biological Chemistry*, 271(52):33632-33638, (1996).

Hill, M.A. and Preiss J., "Functional Analysis of Conserved Histidines in ADP-Glucose Pyrophosphorylase from *Escherichia Coli*" *Biochemical and Biophysical Research Communications*, 244:573-577, (1998).

Hong, B., et al., "Identification of a Calmodulin-Regulated $Ca^{2+}$-ATPase in the Endoplasmic Reticulum," *Plant Physiology*, 119:1165-1175, (1999).

Jauh, G.Y., et al., "Tonoplast Intrinsic Protein Isoforms as Markers for Vacuolar Functions," *The Plant Cell*, 11:1867-1882, (1999).

Kennedy, B.K., el al., "Redistribution of Silencing Proteins From Telomeres to the Nucleolus is Associated With Extension of Life Span in *S. cerevisiae*," *Cell*, 89:381-391, (1997).

Kieber, J.J., et al., "CTR1, a Negative Regulator of the Ethylene Response Pathway in *Arabidopsis*, Encodes a Member of the Raf Family of Protein Kinases," *Cell*, 72:427-441, (1993).

Kirsch, M., et al., "Salt Stress Induces an Increased Expression of V-Type $H^+$-ATPase in Mature Sugar Beet Leaves," *Plant Molecular Biology*, 32:543-547, (1996).

Krysan, P.J., et al., "Identification of Transferred DNA Insertions Within Arabidopsis Genes Involved in Signal Transduction and Ion Transport," *Proc. Natl. Acad. Sci. USA*, 93:8145-8150, (1996).

Lazar, E., et al., "Transforming Growth Factor ⊕: Mutation of Aspartic Acid 47 and Leucine 48 Results in Different Biological Activities," *Molecular and Cellular Biology*. 8(3):1247-1252, (1988).

Levi, M., et al., "Rapid Immunofluorescent Determination of Cells in the S Phase in Pea Root Meristems: An Alternative to Autoradiography," *Physiologic Plantarum*, 71: 68-72, (1987).

Li, J., et al., "Arabidopsis $H^+$-PPase AVP1 Regulates Auxin-Mediated Organ Development," *Science*, 310:121-125, (2005).

Madhani, H.D., el al., "MAP Kinases with Distinct Inhibitory Functions Impart Signaling Specificity During Yeast Differentiation," *Cell*, 91:673-684, (1997).

Madrid, R., et al., "Ectopic Potassium Uptake in trk 1 trk2 Mutants of *Saccharomyces cerevisiae* Correlates With a Highly Hyperpolarized Membrane Potential," *The Journal of Biological Chemistry*, 272(24):14838-14844, (1998).

Marty, F., "The Biogenesis of Vacuoles: Insights from Microscopy," In: Leight RA, Sanders D (eds) The Plant Vacuole, pp. 1-42. Academic Press, San Diego, (1997).

Maeshima, Masayoshi, "Vacuolar $H^+$-Pyrophosphatase," *Biochimica et Biophysica Acta* 1465: 37-51 (2000).

McCormick, S., "Transformation of tomato with *Agrobacterium tumerfaciens*," In: Lindsey, K. (ed) Plant Tissue Culture Manual, pp. 1-9. Kluwer Academic Publishers, Dordrecht, The Netherlands, (1991).

McCusker, J.H. et al., "Pleiotropic Plasma Membrane ATPase Mutations of *Saccharomyces cerevisiae*," *Molecular and Cellular Biology*, 7(11):4082-4088, (1987).

Mitsuda, N., et al., "Pollen-Specific Regulation of Vacuolar $H^+$-PPase Expression by Multiple *cis*-Acting Elements," *Plant Molecular Biology*, 46: 185-192 (2001).

Mullen, R.T., et al., "Identification of the Peroxisomal Targeting Signal for Cottonseed Catalase," *The Plant Journal*, 12(2):313-322, (1997).

Murguia, J.R., et al., "A Salt-Sensitive 3'('),5'-Bisphosphate Nucleotidase Involved in Sulfate Activation," *Science*, 267:232-234, (1995).

Nass, R. and Rao, R., "Novel Localization of a $Na^+/H^+$ Exchanger in a Late Endosomal Compartment of Yeast," *The Journal of Biological Chemistry*, 273(33):21054-21060, (1998).

Nass, R., et al., "Intracellular Sequestration of Sodium by a Novel $Na^+/H^+$ Exchanger in Yeast Is Enhanced by Mutations in the Plasma Membrane $H^+$-ATPase," *The Journal of Biological Chemistry*, 272(42):26145-26152, (1997).

Neuhaus, J.M. and Rogers, J.C., "Sorting of Proteins to Vacuoles in Plant Cells," *Plant Molecular biology*, 38:127-144, (1998).

Niyogi, K.K. and Fink, G.R., "Two Anthranilate Synthase Genes in *Arabidopsis*: Defense-Related Regulation of the Tryptophan Pathway," *The Plant Cell*, 4:721-733, (1992).

Paris, N., et al., "Molecular Cloning and Further Characterization of a Probable Plant Vacuolar Sorting Receptor," *Plant Physiol.*, 115:29-39, (1997).

Park, S., et al., "Up-Regulation of a $H^+$-Pyrophosphatase ($H^+$-PPase) as a Strategy to Engineer Drought-Resistant Crop Plants," *PNAS* 102 (52): 18830-18835 (2005).

Quesada, A., et al., "PCR-Identification of a *Nicotiana plymbaginifolia* cDNA Homologous to the High-Affinity Nitrate Transporters of the crnA Family," *Plant Molecular Biology*, 34:265-274, (1997).

Randall, S.K. and Sze, H., "Properties of the Partially Purified Tonoplast $H^+$-Pumping ATPase From Oat Roots," *The Journal of Biological Chemistry*, 261(3):1364-1371, (1986).

Rate, D.N., et al., "The Gain-of-Function Arabidopsis acd6 Mutant Reveals Novel Regulation and Function of the Salicylic Acid Signaling Pathway in Controlling Cell Death, Defenses, and Cell Growth," *The Plant Cell*, 11:1695-1708, (1999).

Rodriguez-Navarro, A. and Ramos, J., "Dual System for Potassium Transport in *Saccharomyces cerevisiae*," *Journal of Bacteriology*, 159(3):940-945, (1984).

Sandler, S.J., et al., "Inhibition of Gene Expression in Transformed Plants by Antisense RNA," *Plant Molecular Biology*, 11:301-310, (1988).

Sato, M.H., et al., "The AtVAM3 Encodes a Syntaxin-Related Molecule Implicated in the Vacuolar Assembly in *Arabidopsis thaliana*," *The Journal of Biological Chemistry*, 272(39):24530-24535, (1997).

Schneider, B.L., et al., "Use of Polymerase Chain Reaction Epitope Tagging for Protein Tagging in *Saccharomyces cerevisiae*," *Yeast*, 11(13):1265-1274, (1995).

Schwappach, B., et al., "Golgi Localization and Functionally Important Domains in the $Nh_2$ and COOH Terminus for the Yeast CLC Putative Chloride Channel Geflp," *The Journal of Biological Chemistry*, 272(24):15110-15118, (1998).

Sheveleva, E., et al., "Increased Salt and Drought Tolerance by D-Ononitol Production in Transgenic *Nicotiana tabacum* L.," *Plant Physiol.*, 115:1211-1219, (1997).

Sorin, A., et al., "PMR1, a $Ca^{2+}$-AtPase in Yeast Golgi, Has Properties Distinct From Sarco/Endoplasmic Reticulum and Plasma Membrane Calcium Pumps," *The Journal of Biological Chemistry*, 272(15):9895-9901, (1997).

Sugita, K., et al., "A Transformation Vector for the Production of Marker-Free Transgenic Plants Containing a Single Copy Transgene at High Frequency," *Plant Journal*, 22(5): 461-469 (2000).

Tsiantis, M.S., et al., "Salt Regulation of Transcript Levels for the C Subunit of a Leaf Vacuolar $H^+$-ATPase in the Halophyte Mesembryanthemum Crystallinum," *The Plant Journal*, 9(5):729-736, (1996).

van der Krol, A.R., et al., "Inhibition of Flower Pigmentation by Antisense CHS Genes: Promoter and Minimal Sequence Requirements for the Antisense Effect," 14:457-466, (1990).

Vitale, A., and Raikhel, N. V., "What do Proteins Need to Reach Different Vacuoles?" *Trends in Plant Science*, 4(4):149-155, (1999).

Wu, S.J., et al., "SOS1, A Genetic Locus Essential for Salt Tolerance and Potassium Acquisition," *The Plant Cell*, 8:617-627, (1996).

Yelenosky, G.C., and Guy, C.L., "Freezing Tolerance of Citrus, Spinach, and Petunia Leaf Tissue," *Plant Physiol.*, 89:444-451, (1989).

Zemo, D.A. and McCabem, J.T., "Transcriptional Responses of the Rat Vasopressin Gene to Acute and Repeated Acute Osmotic Stress," *Neuroscience Research*, 44:45-50, (2002).

Zhen, R.G., et al., "Acidic Residues Necessary for Pyrophosphate-Energized Pumping and Inhibition of the Vacuolar $H^+$-Pyrophosphatase by N,N'-Dicyclohexylcarbodiimide," *The Journal of Biological Chemistry*, 272(35):22340-22348, (1997).

Zhen, R.G., et al., "Aminomethylenediphosphonate: A Potent Type=Specific Inhibitor of Both Plant and Phototrophic Bacterial $H^+$-Pyrophosphatases," *Plant Physiol.*, 104:153-159, (1994).

Zhen, R.G., et al., "Localization of Cytosolically Oriented Maleimide-Reactive Domain of Vacuolar $H^+$-Pyrophosphatase," *The Journal of Biological Chemistry*, 269(37):23342-23350, (1994).

Hung, S., et al., "Vacuolar $H^+$-Pyrophosphatase cDNA (Accession No. U31467) from Etiolated Mung Bean Seedlings," Plant Gene Register PGR 95-082, *Plant Physiol.*, 109:1125-1127 (1995).

Ikeda, M., et al., "A Vacuolar $H^+$-Pyrophosphatase in *Acetabularia acetabulum*: Molecular Cloning and Comparison with Higher Plants and a Bacterium," *J. of Exp. Botany*, 50(330):139-140 (1999).

Maruyama, C., et al., "Structural Studies of the Vacuolar $H^+$-Pyrophosphatase: Sequence Analysis and Identification of the Residues Modified by Fluorescent Cyclohexylcarbodiimide and Maleimide," *Plant Cell Physiol.*, 39(10):1045-1053 (1998).

Nakanishi, Y. et al., "Molecular Cloning and Sequencing of the cDNA for Vacuolar $H^+$-Pyrophosphatase from *Chara corallina*," *Biochimica et Biophysica Acta*, 1418:245-250 (1999).

Nakanishi, Y. and Maeshima, M., "Molecular Cloning of Vacuolar $H^+$-Pyrophosphatase and Its Developmental Expression in Growing Hypocotyl of Mung Bean," *Plant Physiol.*, 116:589-597 (1998).

Sakakibara, Y. et al., "Identification of the Gene Structure and Promoter Region of H+-Translocating Inorganic Pyrophosphatase in Rice (*Oryza sativa L.*)," *Biochimica et Biophysica Acta*, 1444:117-124 (1999).

Sakakibara, Y. et al., "Isolation and Characterization of cDNAs encoding Vacuolar H+-Pyrophosphatase Isoforms From Rice (*Oryza sativa L.*)," *Plant Molecular Biol.*, 31:1029-1038 (1996).

Smart, L.B., et al., "Genes Involved in Osmoregulation During Turgor-Driven Cell Expansion of Developing Cotton Fibers Are Differentially Regulated," *Plant Physiol.*, 116:1539-1549 (1998).

Suzuki, Y., et al., "Molecular Cloning of Vauolar H+-Pyrophosphatase and its Expression During the Development of Pear Fruit," *Plant Cell Physiol.*, 40(8):900-904 (1991).

Tanaka, Y., et al., "Molecular Cloning of cDNA for Vacuolar Membrane Proton-Translocating Inorganic Pyrophosphatase in *Hordeum vulgare*," *Biochem & Biophys. Res. Comm.*, 190(3):1110-1114 (1993).

Barkla, B.J. and Pantoja, O., "Physiology of Ion Transport Across the Tonoplast of Higher Plants," *Annu. Rev. Plant Physiol. Plant Mol. Biol.*, 47:159-184 (1996).

Kay, R., et al., "Duplication of CaMV 35S promoter sequences creates a strong enhancer for plant genes," *Science*, 236:1299-1302 (1987).

Final Office Action, 11/119,683, mailed Mar. 16, 2010.
Office Action, 11/119,683, mailed Sep. 17, 2009.
Office Action, 11/119,683, mailed Jul. 18, 2008.
Office Action, 11/119,683, mailed Nov. 30, 2007.
Final Office Action, 11/119,683, mailed Jul. 10, 2007.
Office Action, 11/119,683, mailed Oct. 5, 2006.
Office Action( Rest. Req), 11/119,683, mailed Jun. 14, 2006.
Final Office Action, 11/890,795, mailed May 26, 2010.
Office Action, 11/890,795, mailed Oct. 13, 2009.
Final Office Action, 11/890,795, mailed Apr. 29, 2009.
Office Action, 11/890,795, mailed Sep. 15, 2008.
Office Action (Rest. Req.), 11/890,795, mailed May 8, 2008.
Office Action (Rest. Req.), 12/384,115, mailed Oct. 16, 2009.
Office Action, 12/384,115, mailed Feb. 24, 2010.
Office Action, 12/384,115, mailed Sep. 16, 2010.
Notice of Allowance, U.S. Appl. No. 11/119,683, Dated: Sep. 15, 2011.
Office Action, CA 2,419,901, dated Nov. 18, 2010.
Office Action, CA 2,419,901, dated Mar. 16, 2009.
Office Action, CA 2,390,719, dated Nov. 12, 2010.
Office Action, CA 2,390,719, dated Mar. 10, 2009.
Office Action, CA 2,418,127, dated Nov. 12, 2010.
Office Action, CA 2,418,127, dated Mar. 10, 2009.
International Search Report and Written Opinion, PCT/US2008/009091, mailed: Oct. 30, 2008.
Notification Concerning Transmittal of International Preliminary Report on Patentability with IPRP, PCT/US2008/009091, mailed: Feb. 9, 2010.
International Search Report, PCT/US01/41806, mailed Dec. 19, 2001.
International Preliminary Examination Report, PCT/US01/41806, mailed Jun. 17, 2003.
International Search Report, PCT/US01/09548, mailed Jul. 31, 2001.
International Preliminary Examination Report (IPER), PCT/US01/09548, mailed Aug. 1, 2003.

Abdullah, R., et al., "Efficient Plant Regeneration From Rice Protoplasts Through Somatic Embryogenesis," *Bio/Technology*, 4:1087-1090 (1986).

Abel, S., et al., "Phosphate Sensing in Higher Plants," *Physiol. Plant.*, 115:1-8 (2002).

Altschul, S.F., et al., "Gapped BLAST and PSI-BLAST: A New Generation of Protein Database Search Programs," *Nucleic Acids Research*, 25(17):3389-3402, (1997).

Arango, M., et al., "The Plasma Membrane Proton Pump ATPase: The Significance of Gene Subfamilies," *Planta*, 216:355-365 (2003).

Bouche-Pillon, et al., "Immunolocalization of the Plasma Membrane H+-ATPase in Minor Veins of Vicia faba in Relation to Phloem Loading," *Plant Physiol.*, 105:691-697 (1994).

Bremberger, C., et al., "Separation and purification of the tonoplast ATPase and pyrophosphatase from plants with constitutive and inducible Crassulacean acid metabolism", *Planta*, vol. 175, Springer-Verlag, pp. 465-470, 1988.

Brini, F., et al., "Cloning and Characterization of a Wheat Vacuolar Cation/Proton Antiporter and Pyrophosphatase Proton Pump," *Plant Physiology and Biochemistry*, 43(4): 347-354 (Apr. 2005).

Cao, J., et al., "Regeneration of Herbicide Resistant Transgenic Rice Plant Following Microprojectilemediated Transformation of Suspension Culture Cells," *Plant Cell Rep.*, 11:589-591 (1992).

Clough, S.J. and Bent, A.F. "Floral Dip: A Simplified Method for Agrobacterium-Mediated Transformation of *Arabidopsis thaliana*," *Plant J.*, 16:735-743 (1998).

Drozdowicz, Y.M. and Rea, P.A., "Vacuolar H+-Pyrophosphatases: From Evolutionary Backwaters Into Mainstream," *Trends Plant Sci.*, 6(5):206-211 (2001).

Estelle, M. and Somerville, C., "Auxin-Resistant Mutants of *Arabidopsis thaliana* with an Altered Morphology," *Mol. Gen. Genet.*, 206:200-206 (1987).

Gahoonia, T.S. and Nielsen, N. E., "Root Traits as Tools for Creating Phosphorus Efficient Crop Varieties," *Plant Soil*, 260:47-57 (2004).

Gaxiola, R., et al., "Increased Size, Salt and Drought Tolerance in *A. thaliana* Overexpressing AVP1 Vacuolar H+- Pyrophosphatase," *Plant Biology*, (Jul. 2001)[online], Retrieved from the Internet: URL: <http://abstracts.aspb.org/pub2001/public/P32/0206.html>.

Gaxiola, R., et al., "Ectopic Overexpression in Tomato of the Arabidopsis AVP1 Gene Results in Drought Tolerance," *Plant Biology*, (Jul. 2003) [online], Retrieved from the Internet: URL: <http//abstracts.aspb.org/pb2003/public/P33/0948.html>.

Gaxiola, R.A., et al., "Plant Proton Pumps," *FEBS Lett.*, 581:2204-2214 (2007).

Gillooly, J.F., et al., "The Metabolic Basis of Whole-Organism RNA and Phosphorus Content," *Proc. Natl. Acad. Sci. USA*, 102(33):11923-11927 (2005).

Hammond, J.P., et al., "Genetic Responses to Phosphorus Deficiency," *Ann. Bot.*, 94:323-332 (2004).

Härtel, H., et al., "DGD1-Independent Biosynthesis of Extraplastidic Galactolipids After Phosphate Deprivation in Arabidopsis?," *Proc. Natl. Acad. Sci. USA*, 97(19):10649-10654 (2000).

Hermans, C., et al., "How Do Plants Respond to Nutrient Shortage by Biomass Allocation?," *Trends Plant Sci.*, 11(12):610-617 (2006).

Holford, I.C.R., "Soil Phosphorus: Its Measurements and Its Uptake by Plants," *Aust. J. Soil Res.*, 35:227-239 (1997).

Kausch, A.P., et al., "Effects of Microprojectile Bombardment on Embryogenic Suspension Cell Cultures of Maize (*Zea mays L.*) Used for Genetic Transformation," *Planta*, 196:501-509 (1995).

Kochian, L., et al., "How Do Crop Plants Tolerate Acid Soils? Mechanisms of Aluminium Tolerance and Phosphorus Efficiency," *Annu. Rev. Plant Biol.*, 55:459-493 (2004).

López-Bucio, et al., "Phosphate Availability Alters Architecture and Causes Changes in Hormone Sensitivity in the Arabidopsis Root System," *Plant Physiol.*, 129:244-256 (2002).

McSteen, P. and Leyser, O., "Shoot Branching," *Annu. Rev. Plant Biol.*, 56:353-374 (2005).

Meyerowitz, E.M., et al., "In Situ Hybridization to RNA in Plant Tissue," *Plant Molec. Biol. Rep.*, 5:242-250, (1987).

Misson, J., et al., "A Genome-Wide Transcriptional Analysis Using *Arabidopsis thaliana* Affymetrix Gene Chips Determined Plant Responses to Phosphate Deprivation," *Proc. Nat!. Acad. Sci. USA*, 102(33):11934-11939 (2005).

Muchhal, U.S., et al., "Phosphate Transporters From the Higher Plant *Arabidopsis thaliana*," *Proc. Natl. Acad. Sci. USA*, 93:10519-10523 (1996).

Murashige, T. and Skoog, F., "A Revised Medium for Rapid Growth and Bioassays With Tobacco Tissue Culture," *Physiol. Plant.*, 15:473-497 (1962).

Murphy, A., et al., "Early Copper-Induced Leakage of K+ From Arabidopsis Seedlings Is Mediated by Ion Channels and Coupled to Citrate Efflux," *Plant Physiol.*, 121:1375-1382 (1999).

Murphy, J. and Riley, J.P., "A Modified Single Solution Method for the Determination of Phosphate in Natural Waters," *Anal. Chim. Acta*, 27:31-36 (1962).

Nakamura, Yoshiyuki, et al., "Stimulation of the Extrusion of Protons and H+-ATPase Activities with the Decline in Pyrophosphatase Activity of the Tonoplast in Intact Mung Bean Roots under High- NaCl Stress and Its Relation to External Levels of Ca$^2$+ Ions", *Plant Cell Physiol.*, vol. 33, No. 2, JSPP, pp. 139-149, 1992.

Raghothama, K.G., "Phosphate Acquisition," *Annu. Rev. Plant Physiol. Plant Mol. Biol.*, 50:665-693 (1999).

Rea, P.A., et al., "Vacuolar H(+)-Translocating Pyrophosphatases: A New Category of Ion Translocase," *Trends Biochem. Sci.*, 17:348-353 (1992).

Sánchez-Calderón, L., et al., "Characterization of Low Phosphorus Insensitive Mutants Reveals a Crosstalk Between Low Phosphorus-Induced Determinate Root Development and Activation of Genes Involved in the Adaptation of Arabidopsis to Phosphorus Deficiency," *Plant Physiol.*, 140:879-889 (2006).

Sarafian, V., et al., "Radiation-Inactivation Analysis of Vacuolar Proton Atpase and Proton Pyrophosphatase From *Beta-Vulgaris L*. Functional sizes for Substrate Hydrolysis and for Proton Transport," *Biochemical Journal*, 283(2): 493-497 (1992).

Shen, H., et al., "Root Plasma Membrane H+-Atpase Is Involved in the Adaptation of Soybean to Phosphorus Starvation," *J. Exp. Bot.*, 57(6):1353-1362 (2006).

Vance, C.P., et al., "Phosphorus Acquisition and Use: Critical Adaptations by Plants for Securing a Nonrenewable Resource," *New Phytologist*, 157:423-447 (2003).

Ward, J., et al., "Dissociation and Reassembly of the Vacuolar H+-ATPase Complex From Oat Roots," *Plant Physiol.*, 99:161-169 (1992).

Xiang, C., et al., "A Mini Binary Vector Series for Plant Transformation," *Plant Mol. Biol.*, 40:711-717 (1999).

Yan, F., et al., "Adaptation of H+-Pumping and Plasma Membrane H+ ATPase Activity in Proteoid Roots of White Lupin Under Phosphate Deficiency," *Plant Physiol.*, 129:50-63 (2002).

Zhang, J., et al., "Improving Drought Tolerance in Medicago Truncatula Via Translational Genomics,", (Jul. 2007)[online] Retrieved from the Internet: URL: <http://abstracts.aspb.org/pb2007/public/P09/P09019.html>.

Zhen, R.G., et al., "The Molecular and Biochemical Basis of Pyrophosphate-Energized Proton Translocation at the Vacuolar Membrane," *Advances in Botanical Research, the Plant Vacuole*, 25:298-337, (1997).

Zhu, Y., et al., "A Link Between Citrate and Proton Release by Proteoid Roots of White Lupin (*Lupinus albus L.*) Grown Under Phosphorus-Deficient Conditions," *Plant Cell Physiol.*, 46(6):892-901 (2005).

Notice of Abandonment, U.S. Appl. No. 09/934,088, Dated: Jul. 27, 2005.

Office Action, U.S. Appl. No. 09/934,088, Dated: Dec. 22, 2004.

Office Action, U.S. Appl. No. 09/934,088, Dated: Sep. 24, 2003.

Office Action, U.S. Appl. No. 11/119,683, Dated: Apr. 11, 2011.

Office Action-Pre Appeal Conf. Decision, U.S. Appl. No. 11/119,683, Dated: Sep. 16, 2010.

Office Action-Pre Appeal Conf. Decision, U.S. Appl. No. 11/119,683, Dated: Mar. 4, 2009.

Notice of Allowance, U.S. Appl. No. 10/344,658, Dated: Jan. 16, 2009.

Office Action—Advisory Action, U.S. Appl. No. 10/344,658, Dated: Dec. 9, 2008.

Office Action—Interview Summary, U.S. Appl. No. 10/344,658, Dated: Oct. 27, 2008.

Office Action, U.S. Appl. No. 10/344,658, Dated: Sep. 18, 2008.

Examiner-Initiated Interview Summary—Office Action, U.S. Appl. No. 10/344,658, Dated: Mar. 18, 2008.

Office Action Made Final, U.S. Appl. No. 10/344,658, Dated: Mar. 10, 2008.

Office Action, U.S. Appl. No. 10/344,658, Dated: Aug. 6, 2007.

Office Action, U.S. Appl. No. 10/344,658, Dated: Nov. 14, 2006.

Interview Summary—Office Action, U.S. Appl. No. 10/344,658, Dated: Aug. 1, 2006.

Office Action Made Final, U.S. Appl. No. 10/344,658, Dated: May 17, 2006.

Office Action, U.S. Appl. No. 10/344,658, Dated: Nov. 3, 2005.

Office Action—Notice of Panel Decision from Pre-Appeal Brief Review, U.S. Appl. No. 11/890,795, Dated: Mar. 28, 2011.

Notice of Allowance, U.S. Appl. No. 12/384,115, dated May 27, 2011.

\* cited by examiner

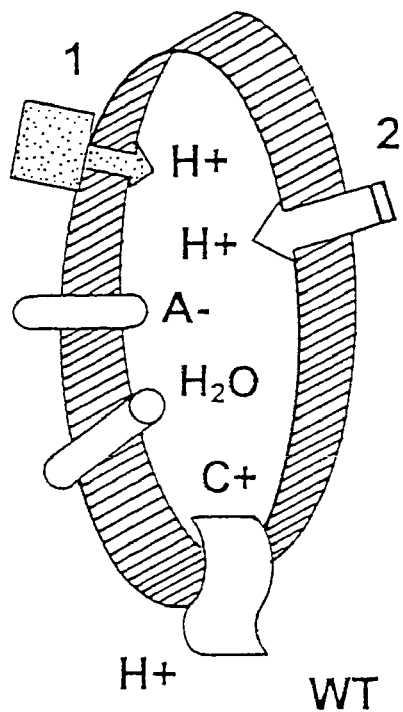
FIG. 8A  WT Vacuole
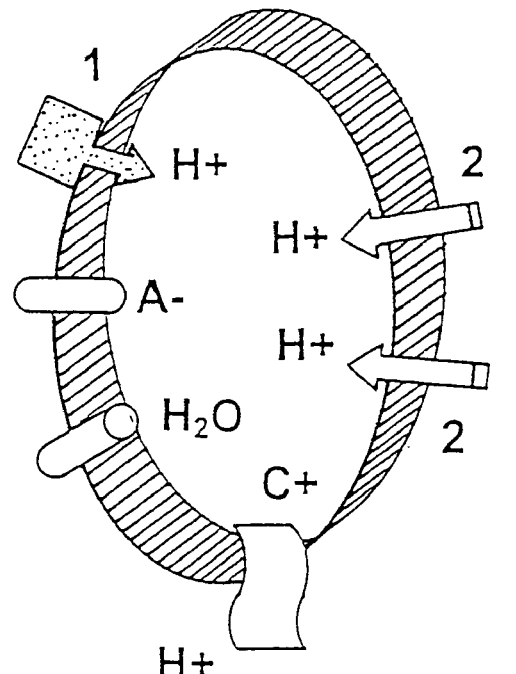
FIG. 8B  35-S AVP-1 Vacuole

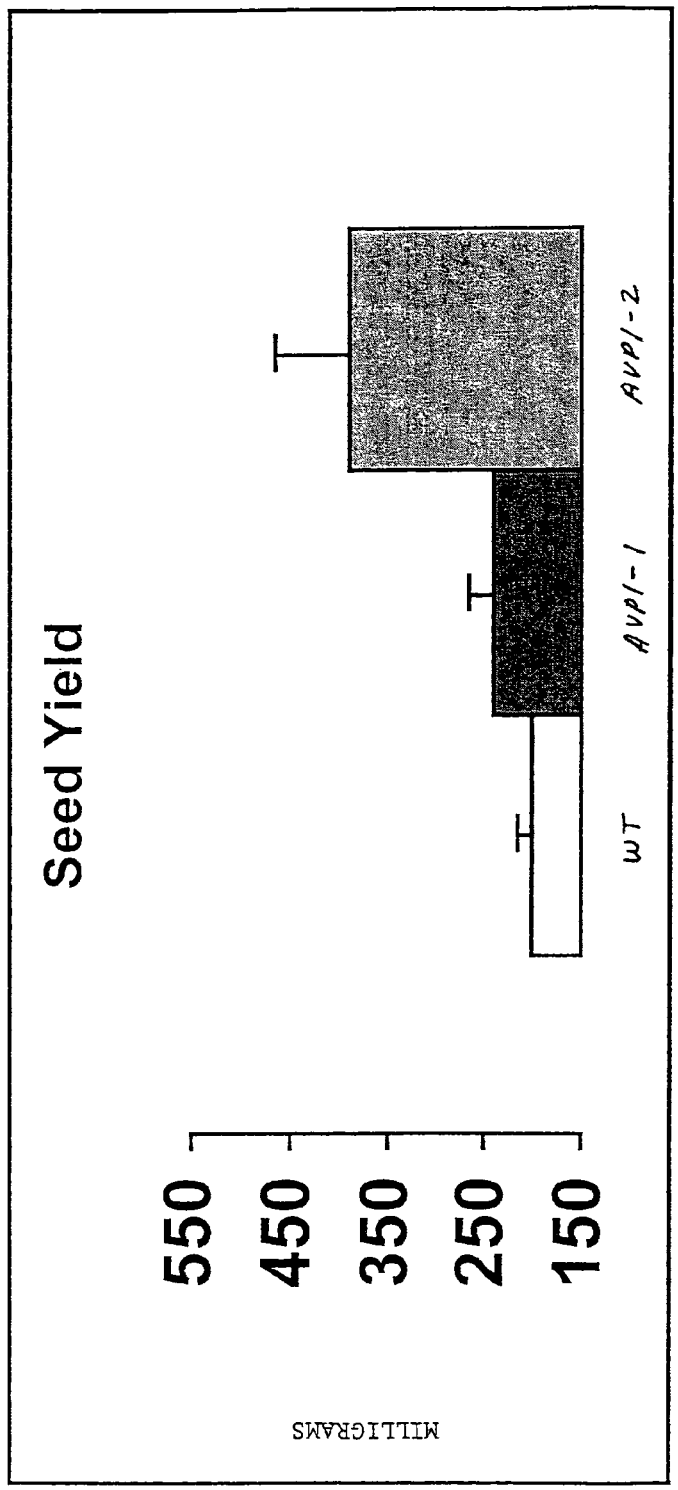
Figure 9. Seed yield.
Wild type, *AVP1-1* and *AVP1-2* transgenic plants were grown in a 16 hour light / 8 hour dark cycle for two months. Seeds were harvest and weighted. Values are means +/- SD (n = 7).

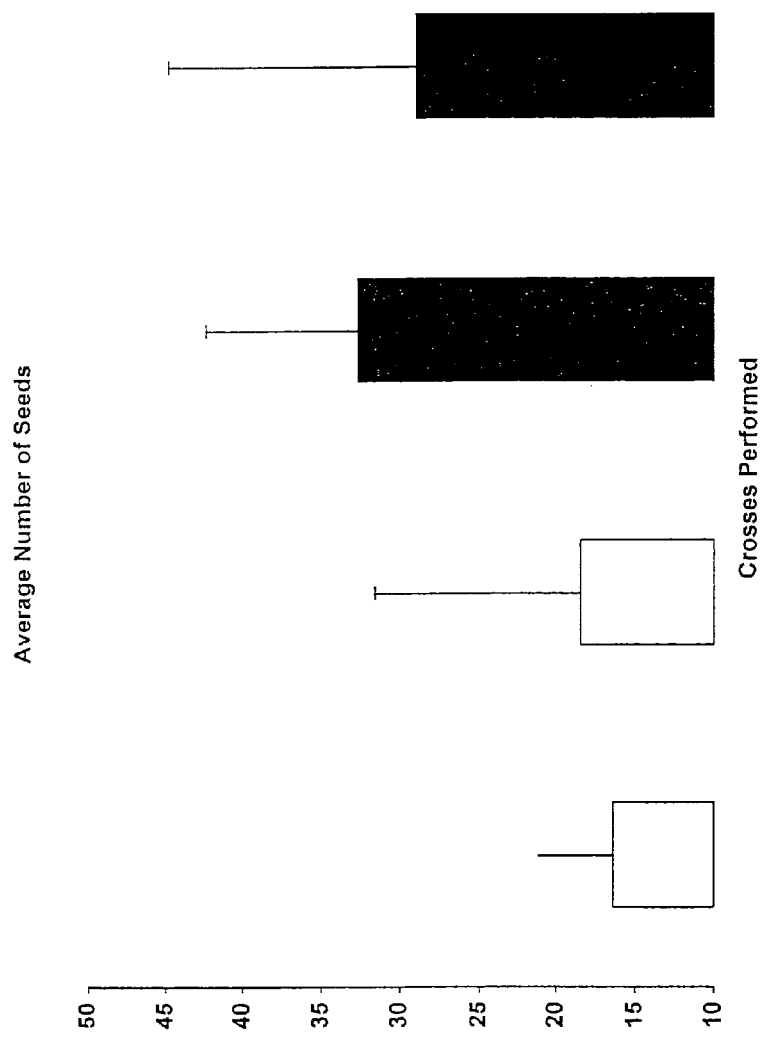
Figure 10A. Average number of seeds. Pollen from wild type plants was used for pollination of transgenic *AVP1-1* and *AVP1-2* lines (white bars). Pollen from the above transgenic plants was used for pollination of wild type plants (black bars). Values are means +/- SD (n = 10).

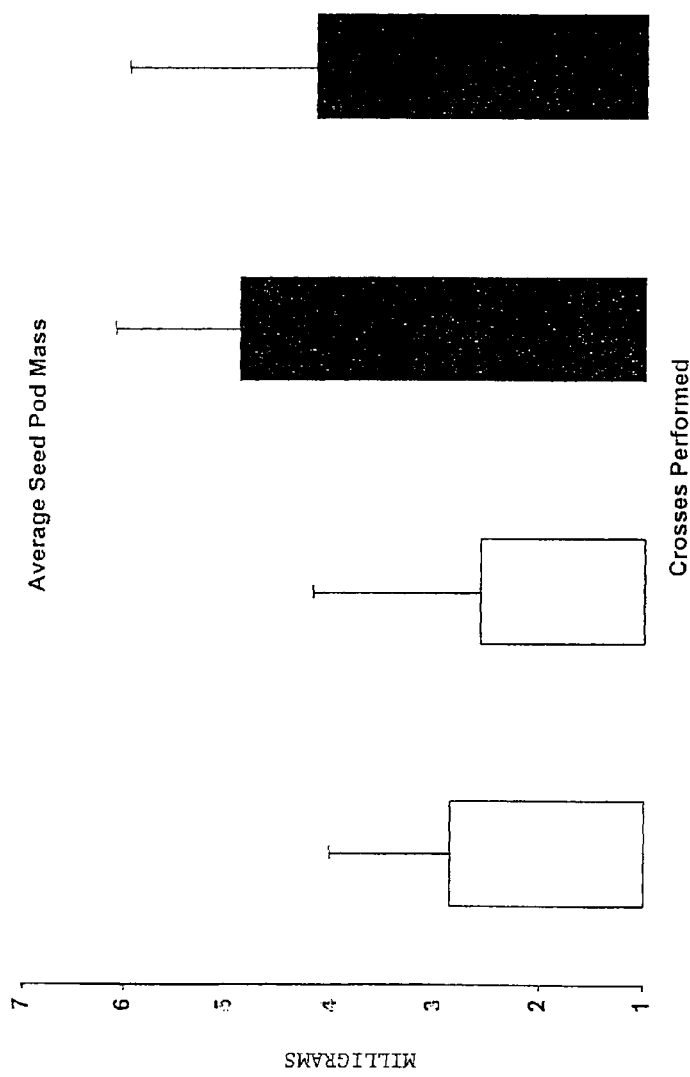
Figure 10B. Average seed pod mass. Pollen from wild type plants was used for pollination of transgenic *AVP1-1* and *AVP1-2* lines (white bars). Pollen from the above transgenic plants was used for pollination of wild type plants (black bars). Values are means +/- SD (n = 10).

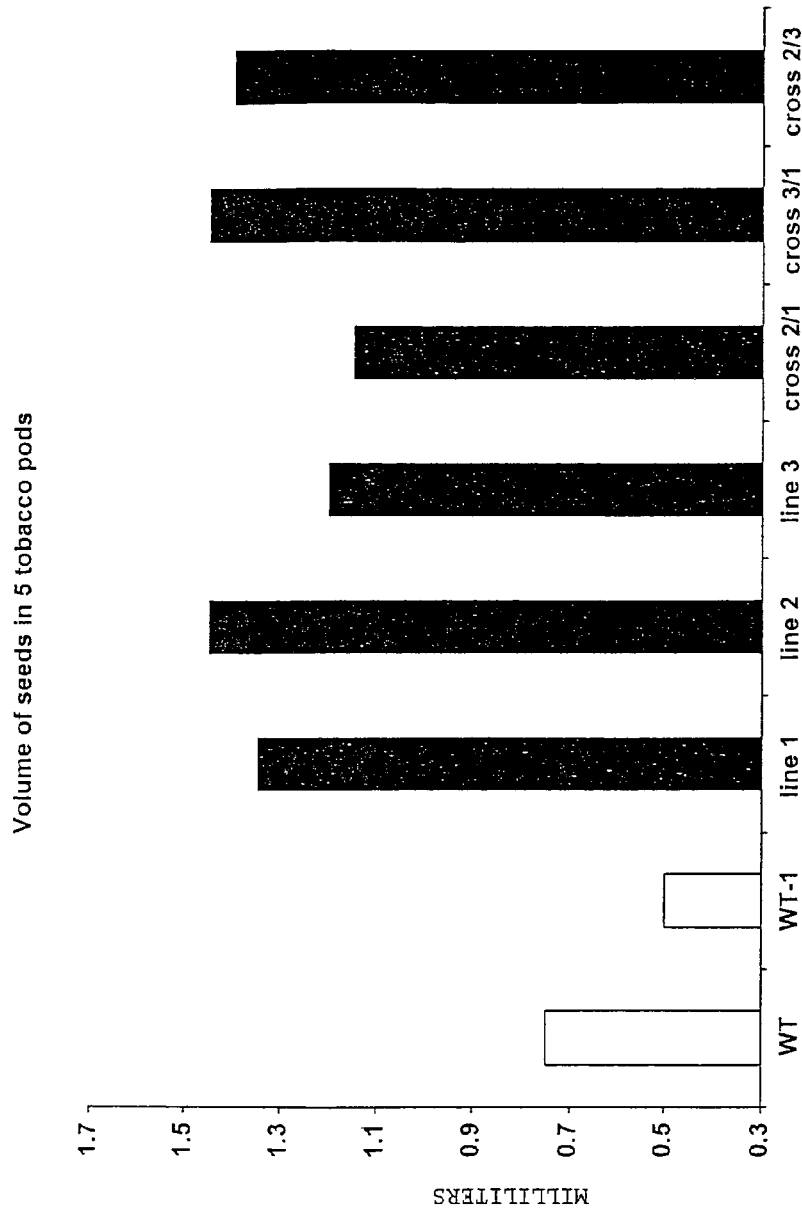
Figure 11. Volume occupied by seeds from wild type and transgenic tobacco.
Five seed pods from wild type (white bars) and *AVP1* transgenic plants (black bars) were collected in eppendorf tubes, and their volume determined.

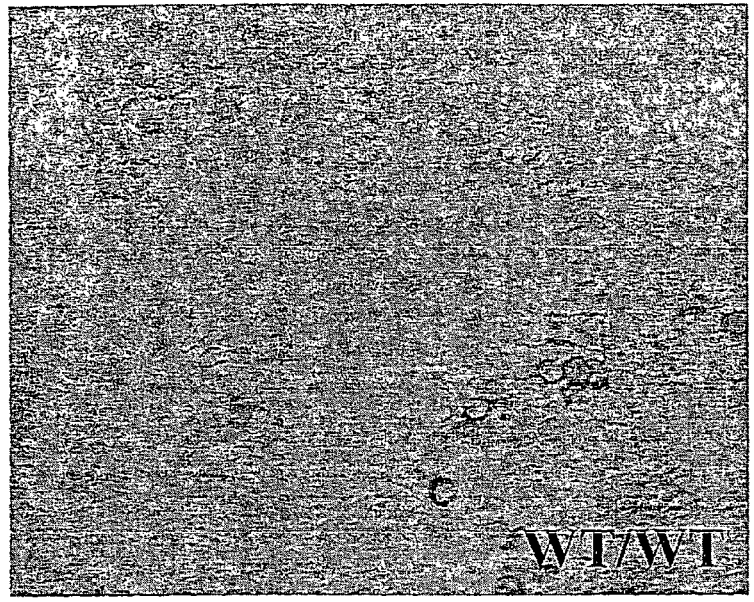
Fig. 12A Photomicrograph (40x) showing formation of pollen tubes in the papillae of the stigma of a wild type Arabidopsis thaliana plant pollinated with wild type pollen.
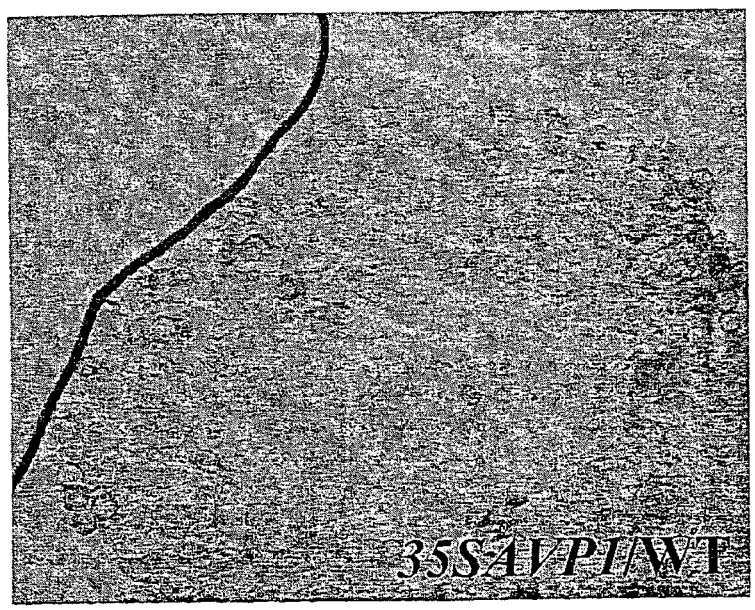
Fig. 12B Photomicrograph (40x) showing formation of pollen tubes in the papillae of the stigma of a wild type Arabidopsis thaliana plant pollinated with 35S AVP1 transgenic pollen.

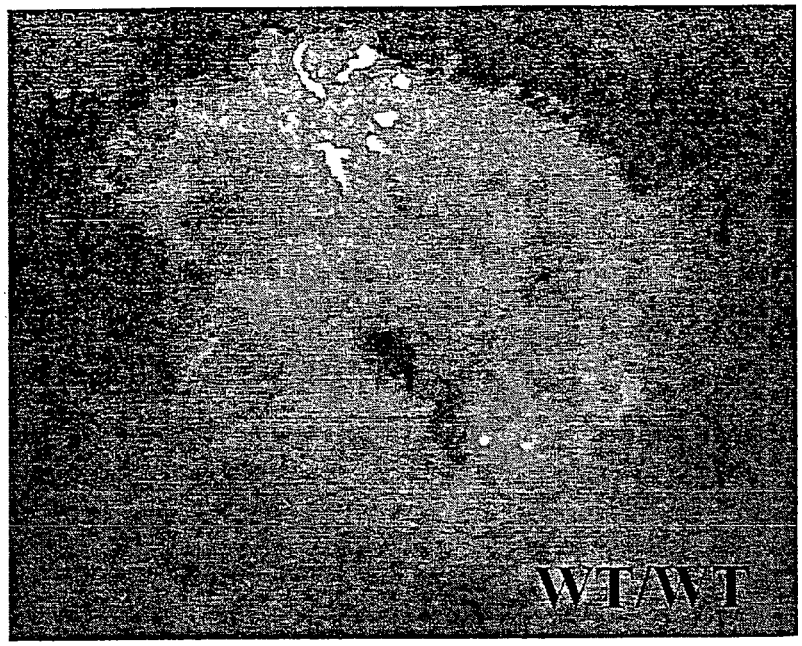
Fig. *13A* Photomicrograph (40x) showing fluorescence of wild type tube forming pollen in wild type Arabidopsis thaliana plant six hours after application, stained using theaniline blue.
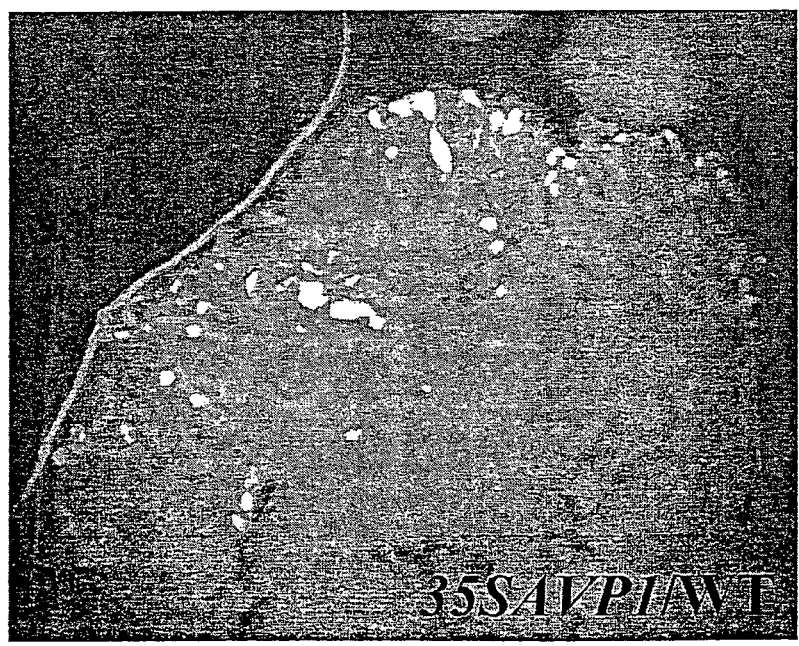
Fig. *13B* Photomicrograph (40x) showing fluorescence of 35S AVP1 tube forming pollen in wild type Arabidopsis thaliana plant six hours after application, stained using theaniline blue.

```
-155        CTTAGATTTATCTTTGAGTCCCGAAACATCGAGGAACGCCTTCGAATCCCTCTCTCTCTGTGTGTTCTCTGTGTTCTCTCTCTCGCC      -67
 -66        CGAAGCGGTTCTCTTTCTTTTGTTTATTTGTTTTTATTTGTTTTTCTCTTATACGGAGGAGAGAAGATGGTGGCGCCTGCTTTGTTACCGGAC       27
                                                                          1-MetValAlaProAlaLeuLeuProGlu        9
 28         CTCTGGACGGAGATCCTTGTACCGATTTGTGCGGTGATTGGTATCGCCTTTTCGCTTTTCCAATGGTACGTTGTATCTCGCGTGAAACTCACC      120
 10         LeuTrpThrGluIleLeuValProIleCysAlaValIleGlyIleAlaPheSerLeuPheGlnTrpTyrValValSerArgValLysLeuThr      40
121         TCTGACCTCGGCCGCCATCGTCTTCCGGTGGAGCTAACAATGGGAAGAATGGATACGGTGATTATCTAATCGAGGAAGAGGAAGGTGTTAATGAC     213
 41         SerAspLeuGlyAlaSerSerSerGlyGlyAlaAsnAsnGlyLysAsnGlyTyrGlyAspTyrLeuIleGluGluGluGluGlyValAsnAsp      71
213         CAGAGTGTTGTCGCTAAGTGCGCTGAGATTCAGACTGCTTATTTCCGAAGGTGCAACTTCATTCCTATTCACGGAGTACAAATATGTTGGTGTC     306
 72         GlnSerValValAlaLysCysAlaGluIleGlnThrAlaIleSerGluGlyAlaThrSerPheLeuPheThrGluTyrLysTyrValGlyVal     102
307         TTCATGATTTTCTTTGCTGCTGTTATCTTTGTTTTCCTCGGCTCTGTTGAGGGATTCAGCACTGATAACAAGCCTTGTACTTACGACACCACC     399
103         PheMetIlePhePheAlaAlaValIlePheValPheLeuGlySerValGluGlyPheSerThrAspAsnLysProCysThrTyrAspThrThr     133
400         AGAACCTGCAAGCCTGCATTGGCTACTGCAGCTTTCAGTACCATTGCTTTCGTGCTTGGTGCTGTTACCTCTGTTCTATCTGGTTTCCTTGGG     492
134         ArgThrCysLysProAlaLeuAlaThrAlaAlaPheSerThrIleAlaPheValLeuGlyAlaValThrSerValLeuSerGlyPheLeuGly     164
493         ATGAAGATTGCTACATACGCTAATGCTACGACCACTTTGGAGGCGAGGAAACGTGTTCGAAAGGCGTTCATTGTTGCATTCAGGTCTGGTGCT     585
165         MetLysIleAlaThrTyrAlaAsnAlaArgThrThrLeuGluAlaArgLysGlyValGlyLysAlaPheIleValAlaPheArgSerGlyAla     195
586         GTGATGGGTTTCCTTCTTGCAGCGAGTGGCTCTATTGGTGCTTTACATTACTATCAATGTGTTCAAGATCTATTACGGAGATGACTGGGAAGGT     678
196         ValMetGlyPheLeuLeuAlaAlaSerGlyLeuLeuValLeuTyrIleThrIleAsnValPheLysIleTyrTyrGlyAspAspTrpGluGly     226
679         CTTTTTGAGGCTATTACTGGTTATGGTCTTGGTGGGTCTTCCATGGCTCTCTTTGGCCGTGTTGGTGGTGGGATCTACACTAAGGCTGCTGAT     771
227         LeuPheGluAlaIleThrGlyTyrGlyLeuGlyGlySerSerMetAlaLeuPheGlyArgValGlyGlyGlyIleTyrThrLysAlaAlaAsp     257
772         GTCGGCGCTGACCTTGTCGGTAAAATTGAGAGGAATATTCCAGAGGATGATCCAAGAAACCCAGCTGTCATTGCTGATAATGTCGGTGACAAT     864
258         ValGlyAlaAspLeuValGlyLysIleGluArgAsnIleProGluAspAspProArgAsnProAlaValIleAlaAspAsnValGlyAspAsn     288
865         GTTGGTGACATTGCTGGTATGGGATCTGATCTCTTTGGATCATATGCTGAAGCATCATGCGCTGCTCTTGTTGTTGCCTCGATCTCATCTTTC     957
289         ValGlyAspIleAlaGlyMetGlySerAspLeuPheGlySerTyrAlaGluAlaSerCysAlaAlaLeuValValAlaSerIleSerSerPhe     319
958         GGAATCAACCACGACTTCACTGCCATGTGCTACCCATTGCTGCTCATCAGTTCAATGGGAATCTTGGTTTGTTTGATCACAACTCTCTTTGCCACT    1050
320         GlyIleAsnHisAspPheThrAlaMetCysTyrProLeuLeuIleSerSerMetGlyIleLeuValCysLeuIleThrThrLeuPheAlaThr     350
1051        GACTTCTTTGAGATTAAGCTTGTCAAGGAGATTGAACCAGCATTGAAGAACCAGCTCATTATCTCAACTGTTATTATCGACTGTTGGTATTGCT    1143
351         AspPhePheGluIleLysLeuValLysGluIleGluProAlaLeuLysAsnGlnLeuIleIleSerThrValIleMetThrValGlyIleAla     381
1144        ATTGTGTCATGGGTTGGCTTACCGACCTCCTTTACCATCTTCAACTTTGGAACACAAAAAGTTGTCAAGAACTGGCAGCTATTCCTTTGTGTT    1236
382         IleValSerTrpValGlyLeuProThrSerPheThrIlePheAsnPheGlyThrGlnLysValValLysAsnTrpGlnLeuPheLeuCysVal     412
1237        TGTGTTGGTCTTTGGGCTGGACTCATTATTGGTTTCGTCACTGAGTACTACACTAGTAACGCCTACAGCCCTGTGCAAGATGTTGCAGATTCA    1329
413         CysValGlyLeuTrpAlaGlyLeuIleIleGlyPheValThrGluTyrTyrThrSerAsnAlaTyrSerProValGlnAspValAlaAspSer     443
1330        TGCAGAACTGGTGCAGCTACCAATGTTATCTTCGGGCTTGCTCTTGGTTACAAATCCGTCATTATTCCAATCTTTGCTATTGCTATCAGTATA    1422
444         CysArgThrGlyAlaAlaThrAsnValIlePheGlyLeuAlaLeuGlyTyrLysSerValIleIleProIlePheAlaIleAlaIleSerIle     474
1423         TTCGTTAGCTTCAGCTTTGCTGCTATGTATGGTGTTGCTGTTGCTGCTCTTGGTATGCTCAGTACCATTGCCACTGGTTTGGCAATTGATGCT    1515
475         PheValSerPheSerPheAlaAlaMetTyrGlyValAlaValAlaLeuGlyMetLeuSerThrIleAlaThrGlyLeuAlaIleAspAlaAla     505
1516        TATGCTCCCATCAGTGACAATGCTGGTGGTATTCCTGAAATGGCTGGAATGAGCCACCGCATCCGTGAAAGAACTGATGCTCTTCATGCCCCT    1608
506         TyrGlyProIleSerAspAsnAlaGlyGlyIleAlaGluMetAlaGlyMetSerHisArgIleArgGluArgThrAspAlaLeuAspAlaAla     536
1609        GGAAACACCACTGCTGCTATTGGAAAGGGATTTGCCATTGGCTCTGCTGCCCTAGTCTCCTTGGCTCTCTTTGGTGCCTTTGTGAGCCGTGCA    1701
537         GlyAsnThrThrAlaAlaIleGlyLysGlyPheAlaIleGlySerAlaAlaLeuValSerLeuAlaLeuPheGlyAlaPheValSerArgAla     567
1702        GGGATCCACACCGTAGATGTTTTGACCCCTAAAGTTATCATTGGGCTCCTTGTTGGTGCCATGCTTCCTTACTGGTTCTCTGCCATGACAATG    1794
568         GlyIleHisThrValAspValLeuThrProLysValIleIleGlyLeuLeuValGlyAlaMetLeuProTyrTrpPheSerAlaMetThrMet     598
1795        AAGAGTGTGGGAAGTGCAGCTCTTAAGATGGTTGAAGAAGTTCGCAGGCAGTTCAACACCATCCCTGGACTTATGGAAGGAACCGCAAAACCA    1887
599         LysSerValGlySerAlaAlaLeuLysMetValGluGluValArgArgGlnPheAsnThrIleProGlyLeuMetGluGlyThrAlaLysPro     629
1888        GACTACGCCACATGTGTCAAGATCTCCACCGATGCTTCCATCAAGGAAATGATACCTCCTGGTTGCCTTGTCATGCTCACACCTCTCATTGTT    1980
630         AspTyrAlaThrCysValLysIleSerThrAspAlaSerIleLysGluMetIleProProGlyCysLeuValMetLeuThrProLeuIleVal     660
1981        GGTTTCTTCTTTGGAGTTGAGACCCTCTCTGGTGTCCTCGCCGGATCTCTTGTATCCGGTGTTCAGATCGCCATATCAGCATCTAACACTGGT    2073
661         GlyPhePhePheGlyValGluThrLeuSerGlyValLeuAlaGlySerLeuValSerGlyValGlnIleAlaIleSerAlaSerAsnThrGly     691
2074        GGTGCCTGGGACAACGCCAAGAAATACATCGAGGCTGCTGGAGCACGCAAACAGCCTTGGACCAAACCGTTCAGAGCCACACAAGGCA    2166
692         GlyAlaTrpAspAsnAlaLysLysTyrIleGluAlaGlyValSerGluHisAlaLysSerLeuGlyProGlySerGluProHisLysAla     722
2167        GCTCTGATTGGAGACACAATTGGAGACCCATTGAAGGATACTTCAGGACCTTCATTGAACATCCTCATCAAGCTCATGGCTGTTGAGTCTCTT    2259
723         AlaValIleGlyAspThrIleGlyAspProLeuLysAspThrSerGlyProSerLeuAsnIleLeuIleLysLeuMetAlaValGluSerLeu     753
2260        GTCTTTGCTCCCTTCTTCGCCACTCACGGTGGTATCCTTTTCAAGTACTTCTAAACTCAATCCGAGGGAAGAAGATGACGATGATGAAGAAGA    2352
754         ValPheAlaProPhePheAlaThrHisGlyGlyIleLeuPheLysTyrPhe-770
2353        AGAAGATGATGATGGCGATCGATTCTAAACTTTCTTTTTTACCATTCTTATTTTCGTTTACCGTAGGTGGTAAAAAACCTTTTTCTTGATGA    2445
2446        GGCTCATTTAAAGAACCAACCAAATGATGTTTCTTTCTCACTCTCTGTCTTTCTGTTTTCTTTTTGTTCTGTTTAGAATTTAGAAATCCAC    2538
2539        CAAGTATTCGGTCGAGACTTGTTTTAGCCGTTACTTTCTGCTGCTTATATTTCCTAAATTGGTTGTCTTCTTCGAAACATAATTGGAATTTAT    2631
2632        TGTTACTGTTAGTCTAAAAAAAAAAA 2658
```

TRANSGENIC POLLEN EXPRESSING EXOGENOUS PLANT VACUOLAR PYROPHOSPHATASE AND METHODS FOR INCREASING SEED PRODUCTION IN PLANTS

REFERENCE TO RELATED APPLICATIONS

This application is a continuation of U.S. patent application Ser. No. 09/934,088 filed Aug. 20, 2001 now abandoned which claims benefit, under Title 35, U.S.C. 119(e), of U.S. Application Ser. No. 60/226,223, filed Aug. 18, 2000.

FIELD OF THE INVENTION

The present invention relates, in general, to methods of imparting desirable phenotypic traits in plants transformed with exogenous nucleotide sequences. More specifically, the present invention concerns imparting the ability to withstand external stresses such as drought, extended exposure to sub-freezing temperatures, and high salinity on plants through transformation with exogenous nucleotides encoding a tonoplast pyrophosphate-driven H+ pump. The present invention also concerns methods for increasing the production of seeds in plants by using pollen from genetically-altered plants to fertilize wild type or transgenic plants. The present invention also relates to the pollen produced by genetically altered plants.

BACKGROUND OF THE INVENTION

The prospects for feeding humanity as we enter the new millennium are formidable. Given the every increasing world population, it remains a major goal of agricultural research to improve crop yield. Until recently crop and plant improvements depended on selective breeding of plants having desirable characteristics. Such selective breeding techniques, however, were often less than desirable as many plants had within them heterogeneous genetic complements that did not result in identical desirable traits to their parents.

Recently, advances in molecular biology have allowed mankind to manipulate the germplasm of animals and plants. Genetic engineering of plants entails the isolation and manipulation of genetic material (typically in the form of DNA or RNA) and the subsequent introduction of that genetic material into a plant or plant cells. Such technology has led to the development of plants with increased pest resistance, plants that are capable of expressing pharmaceuticals and other chemical, and plants that express beneficial traits. Advantageously such plants not only contain a gene of interest, but remain fertile and often desirably to pass the gene on to its progeny.

One particular area of interest of late has been the development of plants with improved production of seeds. Improving the yield in the production of seeds from cultivars, such as rice, canola, wheat, corn, and sunflower, can increase food production for animal and human consumption. Also, improved seed yield can have economic benefits by reducing the costs associated with producing seed for farming.

The yield of a plant crop may be improved by growing transgenic plants that are individually larger than the wild-type plant in vegetative and/or reproductive structure. It is known in the art that certain growth factors may be used to increase plant and/or plant flower size. Unfortunately, application of such growth factors is costly and time consuming, and do not necessarily substantially increase the yield of seeds from the plants. A need, therefore, exists for developing an improved method for increasing the yield of seeds from plants.

SUMMARY OF THE INVENTION

In a first embodiment, the present invention provides a transgenic plant resistant to the effects of externally imposed stresses, wherein the transgenic plant comprises a nucleotide sequence comprising an exogenous tonoplast pyrophosphate driven H+ pump gene operably linked to a promoter. The transgenic plant of the invention is resistant to externally imposed stresses such as drought, prolonged exposure to temperatures below 0° C., and growth media high in salt content, where the growth media may be soil or water. Preferably, the exogenous tonoplast driven H+ pump gene is operably linked to a double tandem enhancer of the 35S CaMV promoter. In addition, the present invention contemplates a seed produced by the transgenic plant of the invention, as well as a progeny plant from the seed of the plant of the invention.

In another embodiment, the present invention provides a transgenic plant containing a polynucleotide sequence comprising a multiplicity of exogenous tonoplast pyrophosphate driven H+ pump genes operably linked to a double tandem enhancer of the 35S CaMV promoter, wherein the number of pyrophosphate driven H+ pump genes is sufficient to express a sufficient number of pyrophosphate driven H+ pumps on the vacuolar membranes to impart desirable phenotypic traits to the transgenic plant. Among these phenotypic traits are an ability to resist the effects of externally imposed stresses, wherein the externally imposed stresses to which the plant is resistant are exemplified by drought, prolonged exposure to temperatures below 0° C., and a growth medium high in salt content. The plant of this embodiment of the invention comprises exogenous nucleic acid that encodes AVP1 or, alternatively, an homolog of AVP1. This homolog may be obtained from tobacco, bacteria, tomato or corn. The transgenic plants of this embodiment comprise an AVP1 gene in a construct designed to overexpress AVP1 of designed to down-regulate endogenous pyrophosphatase. In this construct, preferably the AVP1 is operably linked to a double tandem enhancer of a 35S CaMV promoter. Preferably, the AVP1 gene is derived from a wild type plant of the same species from which the transgenic plant is derived. Alternatively, the AVP1 gene is derived from a wild type plant of a different species from which the transgenic plant is derived.

In another aspect of this embodiment of the present invention, the transgenic plant is larger than a wild-type plant of the same species. Also, the invention contemplates a progeny plant of the transgenic plant, seeds produced by the transgenic plant, and a progeny plant grown from the seed.

In yet another embodiment of the invention, the present invention contemplates a transgenic plant obtained by introducing into the genome of the plant exogenous nucleic acid that alters expression of vacuolar pyrophosphatase in the transgenic plant, as well as plant cells comprising exogenous nucleic acid that alters expression of vacuolar pyrophosphatase in the plant cell. Preferably, the plant cells are selected from the group consisting of root cells and stem cells. Furthermore, the plant cells comprise exogenous nucleic that acid encodes the AVP1 protein. Preferably, in the plant cells of the present invention, the exogenous nucleic acid that encodes AVP1 is present in a construct designed to overexpress AVP1 or designed to down-regulate endogenous pyrophosphatase. More preferably, the construct comprises the AVP1 gene operably linked to a chimeric promoter designed to overexpress AVP1. More preferably still, the AVP1 gene is operably linked to a double tandem enhancer of a 35S CaMV promoter. In this embodiment, the nucleotide encoding AVP1 is derived from a wild type plant of the same species from which the transgenic plant is derived, although the present invention also contemplates that the nucleotide encoding AVP1 can be derived from a wild type plant of a different species from which the transgenic plant is derived.

The present invention, in yet another embodiment, provides a method of making a transgenic plant that is larger in size than its corresponding wild type plant comprising introducing into one or more cells of a plant a nucleotide sequence that alters expression of vacuolar pyrophosphatase in the plant to yield transformed cells, thereby producing a transgenic plant that is larger than its corresponding wild type plant. In this embodiment, the method further comprises regenerating plants from the transformed cells to yield transgenic plants and selecting a transgenic plant that is larger than its corresponding wild type plant, thereby producing a transgenic plant which is larger than its corresponding wild type plant. Also encompassed by this embodiment of the present invention is a transgenic plant produced by this method.

In yet another alternative embodiment, the present invention contemplates a method of increasing the yield of a plant comprising introducing into one or more cells of a plant nucleic acid that alters expression of vacuolar pyrophosphatase in the plant to yield transformed cells, thereby increasing the yield of the plant this method further comprises regenerating plants from the transformed cells to yield transgenic plants and selecting a transgenic plant that is larger than its corresponding wild type plant, thereby increasing the yield of the plant.

Also provided by the present invention is a method of making a transgenic plant having increased flower size compared to its corresponding wild type plant comprising introducing into one or more cells of a plant nucleic acid that alters expression of vacuolar pyrophosphatase in the plant to yield transformed cells, thereby producing a transgenic plant having increased flower size compared to its corresponding wild type plant preferably, the exogenous nucleic acid encodes AVP1. This embodiment of the invention also enompasses a transgenic plant produced by the method.

In another embodiment, the invention of the instant application provided a method of making a transgenic plant with increased biomass comprising introducing into one or more cells of a plant a nucleic acid construct that alters expression of vacuolar pyrophosphatase so as to increase vacuolar pyrophosphatase activity in the cell to yield transformed cells thereby producing a transgenic plant with increased biomass. This method further comprises regenerating plants from the transformed cells to yield transgenic plants and selecting a transgenic plant with increased biomass. Also encompassed by this embodiment of the present invention is a transgenic plant produced by the method.

In an alternate aspect of this embodiment, the present invention provides a method of making a transgenic plant with an increased biomass over its corresponding wild type plant, wherein the increased biomass relates to an increase in the biomass of a plant part selected from the group consisting of leaves, stems, roots, seeds, flowers, and fruits; said method comprising introducing into one or more cells of a plant an exogenous nucleic acid that alters expression of vacuolar pyrophosphatase such so as to enhance the activity of the vacuolar pyrophosphatase in the plant to yield transformed cells, thereby producing a transgenic plant with an increased biomass. This method, as provided by the present invention, further comprises regenerating plants from the transformed cells to yield transgenic plants and selecting a transgenic plant that is larger than its corresponding wild type plant, thereby producing a transgenic plant with an increased biomass. Preferably, according to this method, the exogenous nucleic acid encodes AVP1, or a homolog thereof. More preferably, the AVP1, or homolog thereof, is expressed from a construct designed to overexpress AVP1, or the homolog thereof. Preferably, this construct comprises the AVP1 gene, or gene encoding a homolog of AVP1, wherein the gene is operably linked to a chimeric promoter designed to overexpress AVP1. More preferably, the AVP1 gene is operably linked to a chimeric promoter selected from the group consisting of tissue specific promoters, constitutive promoters, inducible promoters and combinations thereof in a most preferred embodiment, the AVP1 gene is operably linked to a tissue-specific promoter that promotes expression of AVP1 in pollen.

In one aspect of this embodiment, the AVP1 gene is operably linked to a double tandem enhancer of a 35S CaMV promoter. Preferably, the AVP1 gene, or homolog thereof, is derived from a wild type plant. Alternatively, the AVP1 gene, or homolog thereof, is derived from a transgenic plant. In yet another aspect of this embodiment, the AVP1 gene, or homolog thereof, is derived from a mutant plant, in one aspect, the transgenic plant is grown in soil, or is grown hydroponically. Also possible, is that a cell from the transgenic plant is grown in culture. Also contemplated by this embodiment of the present invention is a transgenic plant produced by this method.

In still another embodiment, the present invention provides a method of making a transgenic plant having increased root structure compared to its corresponding wild type plant comprising introducing into one or more cells of the plant an exogenous nucleic acid that alters expression of vacuolar pyrophosphatase so as to increase vacuolar pyrophosphatase activity in the plant to yield transformed cells, thereby producing a transgenic plant having increased root structure. According to this embodiment of the present invention, the exogenous nucleic acid encodes AVP1, or a homolog thereof. Also contemplated here is a transgenic plant produced by the method.

In a most preferred embodiment, the present invention contemplates a method for increasing production of seeds in plants comprising the steps of (a) providing pollen from a first plant, wherein said first plant has been transformed with a tonoplast pyrophosphate driven H+ pump gene operably linked to a promoter to create a transgenic plant; (b) fertilizing a second plant of the same species from which the first plant is derived with the pollen from the transgenic plant; and (c) culturing the fertilized plant until the plant produces mature seeds. According to this method, the tonoplast pyrophosphatase driven H+ pump gene transformed into the first plant is exogenous. Also contemplated is that the second plant is a transgenic plant or a wild type plant.

Preferably, the exogenous tonoplast pyrophosphate driven H+ pump gene is operably linked to a chimeric promoter. More preferably, the exogenous tonoplast pyrophosphate driven H+ pump gene is operably linked to a double tandem enhancer of the 35S CaMV promoter. More preferably still, the exogenous tonoplast pyrophosphate driven H+ pump gene is operably linked to a double tandem enhancer of the 35S CaMV promoter and is further operably linked to a multiple cloning site in a most preferred embodiment, the exogenous tonoplast pyrophosphate driven H+ pump gene encodes AVP1. Also coming within this embodiment of the present invention is a plant seed produced by the method; a progeny plant grown from the plant seed, wherein the first and second plants used in the method are from the species *A. thaliana*. Alternatively, the first and second plants are from the species *nicotinia tabacum*.

In another aspect of this embodiment of the invention, the second plant has been transformed with a polynucleotide sequence comprising an exogenous tonoplast pyrophosphatase driven H+ pump gene operably linked to a promoter. Preferably, the polynucleotide sequence comprises an exogenous tonoplast pyrophosphatase driven H+ pump gene operably linked to a double tandem enhancer of the 35S CaMV promoter. Further, the polynucleotide sequence comprises an exogenous tonoplast pyrophosphatase driven H+ pump gene operably linked to a double tandem enhancer of the 35S CaMV promoter and further operably linked to a multiple cloning site. More preferably, the polynucleotide sequence comprises an exogenous tonoplast pyrophosphatase driven H+ pump gene operably linked to a double tandem enhancer of the 35S CaMV promoter and further operably linked to a heterologous coding sequence. This aspect of the present embodiment also contemplates a plant seed produced by the method and a progeny plant grown from the plant seed.

The present invention provides, in one aspect, pollen produced by a transgenic plant that has been transformed with a tonoplast pyrophosphatase driven H+ pump gene operably linked to a promoter. The pollen from these transgenic plants is more competent in fertilization, resulting in increased yield of seeds from the plants. Because most crops of interest are hermaphroditic, self-pollination of the transgenic plants by the more competent pollen will occur and will result in improved seed yield. The improved seed yield is demonstrated both by increased numbers of seeds and increased seed pod mass. Increased seed yield can increase the production of products from cultivars such as rice, canola, wheat, corn and sunflower. Also, increased seed yield can decrease the cost of producing seeds to be used in crop production.

Other advantages of the present invention will become more readily apparent in view of the accompanying detailed description of the invention.

BRIEF DESCRIPTION OF THE DRAWINGS

So that those having ordinary skill in the art to which the subject invention appertains will more readily understand the subject invention, reference may be had to the drawings, wherein:

FIGS. 8A and 8B are illustrations demonstrating the theorized mechanism for a higher accumulation of solids into vacuoles via a proton driven function versus that of WT vacuoles.

FIG. 9 is a graph showing seed yield for wild-type, AVP1-1 and AVP1-2 plants grown in a 16 hour light/8 hour dark cycle for two months.

FIG. 10A is a graph showing average number of seeds.

FIG. 10B is a graph showing average seed pod mass.

FIG. 11 is a graph showing volume occupied by seeds from wild type and transgenic tobacco.

FIG. 12A. is a photomicrograph (40×) showing formation of pollen tubes in the papillae of the stigma of a wild type *Arabidopsis thaliana* plant pollinated with wild type pollen.

FIG. 12B. is a photomicrograph (40×) showing formation of pollen tubes in the papillae of the stigma of a wild type *Arabidopsis thaliana* plant pollinated with 35S AVP1 transgenic pollen.

FIG. 13A. Photomicrograph (40×) showing fluorescence of wild type tube forming pollen in wild type *Arabidopsis thaliana* plant six hours after application, stained using theaniline blue.

FIG. 13B. Photomicrograph (40×) showing fluorescence of 35S AVP1 tube forming pollen in wild type *Arabidopsis thaliana* plant six hours after application, stained using theaniline blue.

FIG. 14. A nucleotide sequence of *Arabidopsis* cDNA (SEQ ID NO:1) encoding *Arabidopsis* vacuolar pyrophosphatase (AVP1) and the predicted amino acid sequence of AVP1 (SEQ ID NO:2) encoded by the nucleotide sequence.

DETAILED DESCRIPTION OF THE INVENTION

Figure 1:
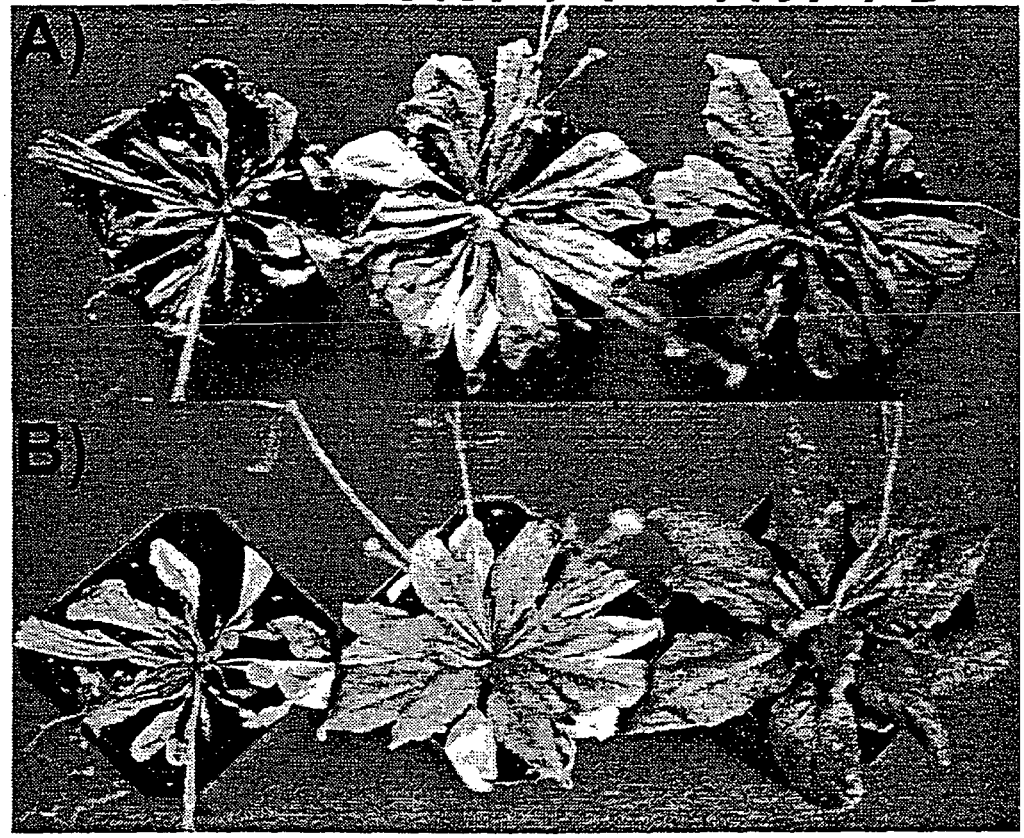
FIG. 1A is an overhead view of wild type (WT) and two independent transgenic lines (AVP1-1 and AVP1-2) after 10 days of water deprivation.
FIG. 1B is an overhead view of the plants shown in FIG. 1A after rewatering.

Preferred embodiments of the invention are described below. The preferred embodiments disclosed herein are to be considered exemplary of the principles of the present invention and are not intended to limit the invention to the embodiments described. Various modifications will be apparent to those skilled in the art based on the teachings herein without departing from the scope or spirit of the invention disclosed herein.

Transgenic plants that overexpress a vacuolar proton-pumping pyrophosphatase have been shown to have improved resistance to stress, such as drought, high salinity or extended exposure to freezing conditions, and to exhibit enhanced meristematic activity. These transgenic plants, and methods for producing these plants, have been described in application Ser. No. PCT/US00/30955, filed on Nov. 10, 2000, and in application Ser. No. PCT/US01/09548, filed on Mar. 24, 2001, the entire contents of each of which are hereby incorporated by reference.

Briefly, this transformation can be accomplished using, for example, an exogenous tonoplast pyrophosphate driven H+ pump gene operably linked to a promoter. The exogenous gene may encode AVP-1 or a homologue of AVP-1. The invention is not limited in this regard, and pollen from any plant that has been transformed to overexpress a vacuolar proton-pumping pyrophosphatase may be used.

The promoter may be a chimeric promoter, a double tandem enhancer of the 355 CaMV promoter, a pollen specific promoter, or any other promoter known to those of skill in the art. Alternatively, the plant may be transformed using a polynucleotide sequence comprising an exogenous tonoplast pyrophosphatase drive H+ pump gene operably linked to a promoter.

The present invention discloses a transgenic plant having upregulated expression of vacuolar pyrophosphatase. It has been found that plants displaying such upregulated activity are, in general larger than wild-type counterparts, demonstrate improved stress resistance to drought and/or freeze, and have increased tolerance to salt in the media in which they are growing.

Any suitable exogenous nucleic acid molecule which alters expression of vacuolar pyrophosphatase in the plant can be used to transform the transgenic plants in accord with the present invention. The exogenous nucleic acid can comprise nucleic acid that encodes a vacuolar pyrophosphatase protein (an exogenous vacuolar pyrophosphatase), such as AVP1, a functional portion thereof (peptide, polypeptide), or a homologue thereof, and/or nucleic acid that alters expression of the endogenous vacuolar pyrophosphatase of the plant into which the exogenous nucleic acid is introduced. By "exogenous nucleic acid" it is meant a nucleic acid from a source other than the plant cell into which it is introduced, or into a plant or plant part from which the transgenic part was produced. The exogenous nucleic acid used for transformation can be RNA or DNA, (e.g., cDNA, genomic DNA). In addition, the exogenous nucleic acid can be circular or linear, double-stranded or single-stranded molecules. Single-stranded nucleic acid can be the sense strand or the anti-sense strand. By a "functional portion" of a nucleic acid that encodes a vacuolar pyrophosphatase protein it is meant a portion of the nucleic acid that encodes a protein or polypeptide which retains a functional characteristic of a vacuolar pyrophosphatase protein. In a particular embodiment, the nucleic acid encodes AVP1, a functional portion or a homologue thereof.

Nucleic acid that alters expression of the endogenous vacuolar pyrophosphatase of the plant into which the exogenous nucleic acid is introduced includes regulatory sequences (e.g., inducible, constitutive) which function in plants and antisense nucleic acid. Examples of regulatory sequences include promoters, enhancers and/or suppressors of vacuolar pyrophosphatase. The nucleic acid can also include, for example, polyadenylation site, reporter gene and/or intron sequences and the like whose presence may not be necessary for function or expression of the nucleic acid but can provide improved expression and/or function of the nucleic acid by affecting, for example, transcription and/or stability (e.g., of mRNA). Such elements can be included in the nucleic acid molecule to obtain optimal performance of the nucleic acid.

The nucleic acid for use in the present invention can be obtained from a variety of sources using known methods. For example, the nucleic acid encoding a vacuolar pyrophosphatase (e.g., AVP1) for use in the present invention can be derived from a natural source, such as tobacco, bacteria, tomato or corn. In one embodiment, the nucleic acid encodes a vacuolar pyrophosphatase that corresponds to a wild type of the transgenic plant. In another embodiment, the nucleic acid encodes a vacuolar pyrophosphatase that does not correspond to a wild type of the transgenic plant. Nucleic acid that alters expression of the endogenous vacuolar pyrophosphatase of the plant into which the exogenous nucleic acid is introduced (e.g., regulatory sequence) can also be chemically synthesized, recombinantly produced and/or obtained from commercial sources.

A variety of methods for introducing the nucleic acid of the present invention into plants are known to those of skill in the art. For example, *Agrobacterium*-mediated plant transformation, particle bombardment, microparticle bombardment (e.g., U.S. Pat. No. 4,945,050; U.S. Pat. No. 5,100,792) protoplast transformation, gene transfer into pollen, injection into reproductive organs and injection into immature embryos can be used. The exogenous nucleic acid can be introduced into any suitable cell(s) of the plant, such a root cell(s), stem cell(s) and/or leaf cell(s) of the plant. In addition, the genetic material of the transformed plant may be introduced into other germ lines displaying traits of interest by cross-breeding the transgenic lines with other lines in accord with established principles of Mendelian genetics.

Any suitable plant can be used to produce the transgenic plants of the present invention. For example, tomato, corn, tobacco, rice, sorghum, cucumber, lettuce, turf grass, ornamental (e.g., larger flowers, larger leaves) and legume plants can be transformed as described herein to produce the transgenic plants of the present invention. In addition, the transgenic plants of the present invention can be grown in any medium which supports plant growth such as soil or water (hydroponically).

Desirable phenotypic traits (e.g., the ability to resist externally imposed stresses, including conditions of decreased water supply or extended periods of below-freezing temperatures) may be introduced into a plant of the present invention by transforming plant cells with exogenous nucleic acid which alters the expression of vacuolar pyrophosphatase in the plant such that expression is upregulated. Any suitable vacuolar pyrophosphatase, several of which have been cloned, can be used in the compositions and methods of the present invention (e.g., Sarafian, V., et al., *Proc. Natl. Acad. Sci., USA,* 89:1775-1779 (1992); Lerchl, J., et al., *Plant Molec. Biol.,* 29: 833-840 (1995); Kim, Y., et al., *Plant Physiol.,* 106:375-382 (1994)). The teachings of Sarafian, V., et al., *Proc. Natl. Acad. Sci., USA,* 89:1775-1779 (1992), Lerchl, J., et al., *Plant Molec. Biol.,* 29: 833-840 (1995), and Kim, Y., et al., *Plant Physiol.,* 106:375-382 (1994), are incorporated by reference herein in their entirety. Sequences of *Arabidopsis* vacuolar pyrophosphatase cDNA (SEQ ID NO:1) and its encoded protein (AVP1; SEQ ID NO:2), both of which were disclosed in Sarafian, V., et al., *Proc. Natl. Acad. Sci., USA,* 89:1775-1779 (1992), are shown in FIG. 14. In a particular embodiment, the present invention relates to a transgenic plant exhibiting desirable phenotypic traits such as resistance to external stresses comprising an exogenous nucleic acid construct which is designed to overexpress AVP1 (Sarafian, V., et al., *Proc. Natl. Acad. Sci., USA,* 89:1775-1779 (1992)). Transformation of the plant cells may be carried out in a whole plant, seeds, leaves, roots or any other plant part. Such transgenic plants are preferably altered such that they grow in a concentration of salt that inhibits growth of a corresponding non-transgenic plant. Transgenic progeny of the transgenic plants, seeds produced by the transgenic plant and progeny transgenic plants grown from the transgenic seed, which are also the subject of the present invention, advantageously carry such salt tolerant trait. Plants may be regenerated from transformed cells to yield transgenic plants, which may be screened for certain levels of salt tolerance. In a preferred embodiment, the exogenous nucleic acid encodes AVP1, or a homologue thereof.

Drought and/or freeze tolerance may be introduced into plants by transforming plant cells with exogenous nucleic acid which alters the expression of vacuolar pyrophosphatase in the plant such that such expression is upregulated. In a preferred embodiment there is provided a substantially drought and/or freeze resistant transgenic plant which comprises a genome having one or more exogenously introduced vacuolar $H^+$-translocating pump genes. A particularly preferred fertile transgenic plant eliciting drought and/or freeze tolerance, as well as the ability to grow in saline soils, comprises an isolated exogenous chimeric DNA construct encoding vacuolar $H^+$-translocating pump, preferably operably linked to a promoter, such as the 35S CaMV promoter or any other promoter, including, without limitation, tissue specific promoters. The transgenic plant may contain a polynucleotide sequence comprising an exogenous tonoplast pyrophosphate $H^+$ pump gene operably linked to a promoter. In yet another particularly preferred drought and/or freeze resistant transgenic plant having the capacity to grow in saline soils, the polynucleotide sequence comprises an exogenous tonoplast pyrophosphate $H^+$ pump gene operably linked to a double tandem enhancer of the 35S promoter. A particularly preferred tonoplast pyrophosphate $H^+$ pump gene is the AVP1 gene.

Previous work has shown that a decrease in the levels of the A subunit of the vacuolar $H^+$-ATPase of carrot, using an antisense construct, resulted in a plant with reduced cell expansion and altered leaf morphology (J. P. Gogarten., et al., The Plant Cell 4, 851-864 (1992)). The present inventor has hypothesized that an increased supply of $H^+$ into the vacuole could cause cell expansion. Recently, based on the theory that as the availability of protons in the vacuolar function of ion accumulation, it has been hypothesized by the same inventor that accumulation of solids in the vacuoles might be useful to protect against draught and to provide for a more freeze resistant plants.

Since plant vacuoles constitute 40 to 99% of the total intracellular volume of a mature plant cell, changes in the size of the vacuole have dramatic effects upon cell size (R. G. Zhen, E. J. Kim, P. A. Rea, in The Plant Vacuole. (Academic Press Limited, 1997), vol. 25, pp. 298-337). The volume of the vacuole is controlled by ion and water fluxes mediated by pumps and transporters. In plants the driving force that triggers the movement of ions, solutes and water across membranes is a proton gradient. The activity of the vacuolar $H^+$-pumps results in luminal acidification and the establishment of a $H^+$ electrochemical potential gradient across the vacuolar membrane, which powers the secondary active transporters of inorganic ions, sugars, and organic acids. The activity of these transporters modulates cellular pH and ion homeostasis and leads to the accumulation of solutes required to generate the osmotic potential that promotes vacuolar expansion (H. Sze, X. Li, M. G. Palmgren, The Plant Cell 11, 677-689 (1999)).

There are three distinct pumps that generate proton electrochemical gradients. One at the plasma membrane that extrudes $H^+$ from the cell (PM $H^+$-ATPase) and two at the vacuolar membrane or other endomembrane compartments that acidify their lumen (the vacuolar type $H^+$-ATPase and $H^+$-PPase) (R. A. Leigh, in The Plant Vacuole L. a. Sanders, Ed. (Academic Press, San Diego, Calif., 1997), vol. 25, pp. 171-194).

The present inventor has recognized that plants have a number of vacuolar $H^+$-translocating pumps, and that by upregulating their activity, increasing their expression, upregulating their transcription and/or translation, or increasing their copy number that one can increase accumulation of solids in the vacuole due to an increase in the availability of protons in the vacuoles. The inventor tested this hypothesis by increasing the copy number of the vacuolar $H^+$-translocating pump, the inorganic pyrophosphatase or V-PPase that consists of a single polypeptide (R. G. Zhen, E. J. Kim, P. A. Rea, in The Plant Vacuole (Academic Press Limited, 1997), vol. 25, pp. 298-337). In Arabidopsis the V-PPase encoded by the AVP-1 gene is capable of generating a $H^+$ gradient across the vacuole membrane (tonoplast) similar in magnitude to that of the vacuolar $H^+$-ATPase (V. Sarafian, Y. Kim, R. J. Poole, P. A. Rea, Proc. Natl. Acad. Sci. 89, 1775-1779 (1992)). As would be understood by one of ordinary skill in the art, similar genes in other plants should function in a similar manner.

It is known that $H^+$-PPase is the main proton pump of vacuolar membranes in growing tissue. The later may be due to the fact that in growing tissue, nucleic acids, DNA, RNAs, proteins and cellulose etc. are actively being synthesized for the construct of the new cells, and as a result, a large amount of PP is produced as a by-product of these metabolic processes. The energy stored in the PP molecule may be transformed into a different source of energy, namely a $H^+$-gradient across the vacuolar membrane. This $H^+$-gradient constitutes the driving force for the vacuolar accumulation of solutes that generate the sufficient osmotic differential that enables the plant cell to initiate growth. While the present invention is not limited in any manner to any particular hypothesis for the increased growth effects seen, the present inventor has hypothesized that in transgenic plants overexpressing AVP-1 that the greater number of $H^+$-$PP_i$ases has a positive effect on the velocity of the generation of the $H^+$ gradient, rendering a more active meristem.

To demonstrate the effect that an increased supply of $H^+$ into the vacuole would have on resistance to drought and/or freeze, and tolerance to salt growth, as well as size of the plants, the present inventor generated transgenic plants containing extra copies of a vacuolar proton pumps AVP-1.

Arabidopsis thaliana plants were transformed with constructs containing the AVP-1 gene. Transgenic lines containing extra copies of this gene were then isolated. The AVP-1, open reading frame was cloned into the Xma1 site of a modified pRT103 [R. Topfer, V. Matzeit, B. Gronenborn, J. Schell and H-H. Steinbiss, Nucleic acid Research 15, 5890 (1987)]. This vector contains a tandem repeat of the 35-S promoter. A HindIII fragment containing the 35-S tandem promoter, AVP-1 ORF and the polyadenylation signal was subcloned into the HindIII site of the pPZP212 vector [P. Hajdukiewicz, Z. Svab and P. Maliga, Plant Molecular Biology 25, 989-994 (1994)]. Agrobacterium-mediated transformation was performed via vacuum infiltration of flowering Arabidopsis thaliana (ecotype columbia). Transgenic plants were selected by plating seeds of the transformed plants on plant nutrient agar plates supplemented with 25 mg/liter kanamycin. Plants were subsequently selected for two generations to identify transgenic plant homozygous for the transgene.

Wild type and AVP1 transgenic plants were tested for drought tolerance by growing the plants under conditions of water deprivation. Plants were grown for four weeks under fully watered regimen at 21° C. (standard culture conditions) and then transferred into a chamber with a 3° C. warmer temperature and no further addition of water. After 10 days of water deprivation (FIG. 1A), plants from each group were rewatered (FIG. 1B). Deprivation of water for this time was lethal to wild type plants, but plants from both transgenic lines, AVP1-1 and AVP1-2, survived and continued normal growth, bolted, and set viable seeds.

Figure 2:
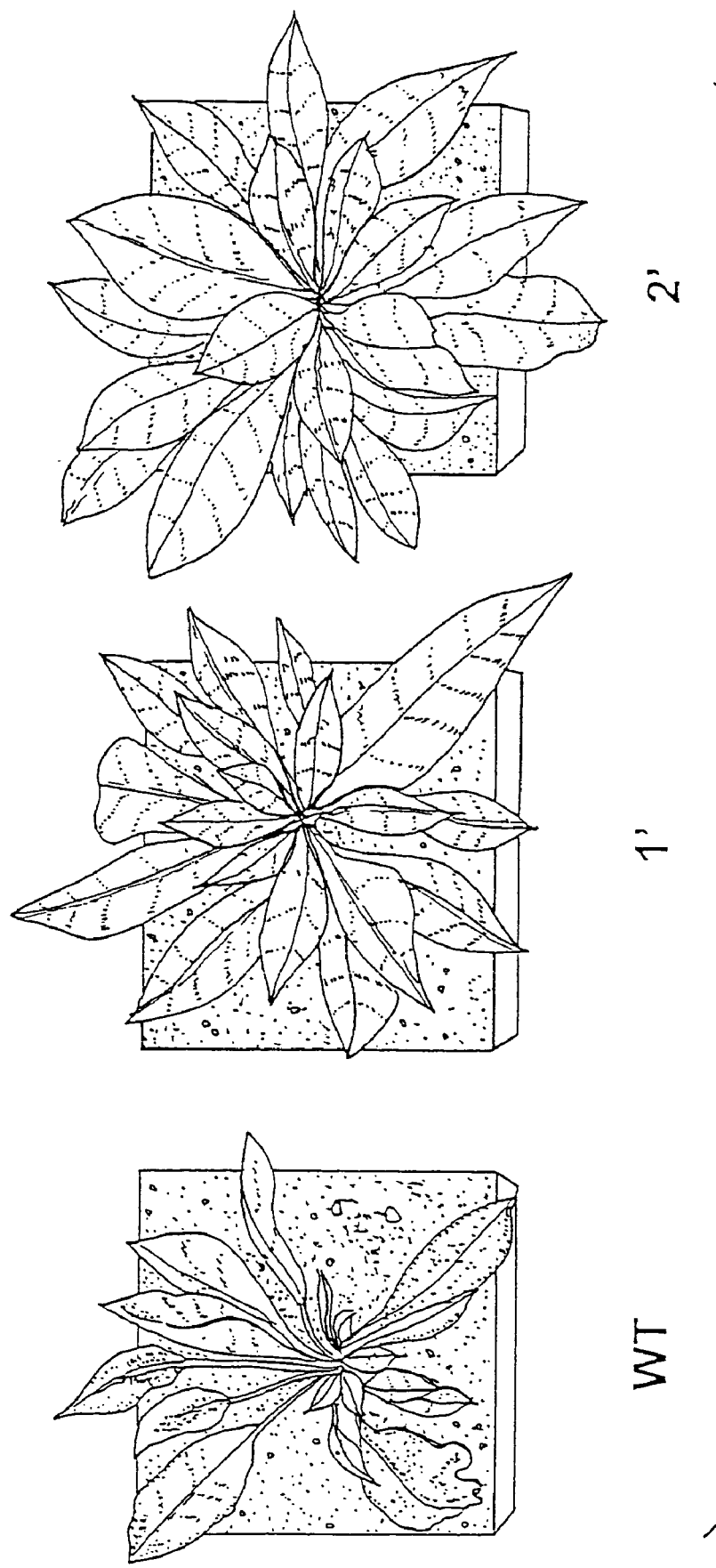
FIG. 2 is an overhead view of a representative wild type plant (WT) versus representative transgenic plants overexpressing AVP1 (AVP1-1 and AVP1-2) after exposure to 7 days of water deficit stress.

FIG. 2 is an overhead view of a representative wild type plant (WT) versus representative transgenic plants overexpressing AVP1 (AVP1-1 and AVP1-2) after exposure to 7 days of water deficit stress. Wild type and transgenic plants overexpressing AVP-1 were tested for drought tolerance (24° C.). After 7 days of water deficit stress wild type (WT) plants withered, whereas plants from both 35S AVP-1 transgenic lines (AVP1-1 and AVP1-2) were turgid and alive. Furthermore, when the drought stressed plants were then watered, transgenic plants pursued normal growth, bolted and set seeds, whereas wild type plants died. The relative water content of leaves from wild type and 35SAVP-1 transgenic plants were determined along the water deficit stress, demonstrating increased water retention by the transgenic lines as compared to the WT plants.

While not illustrated in the accompanying illustrations, similar results may be seen with respect to freeze challenge (<0° C.) over a 24 hour or greater period for a number of plant species. While not limited to such hypothesis, transgenic plants overexpressing AVP1 (AVP1-1 and AVP1-2) are believed to provide enhanced protection from freeze as compared to wild type (WT) plants due to the higher amounts of cations in the vacuoles. Higher amounts of cations confer a greater osmotic pressure that leads to a greater water retention capability endowing the plants not only with the ability to withstand low soil water potentials, but also providing greater protection from freezing that leads to significant desiccation of the plants.

Figure 3A:
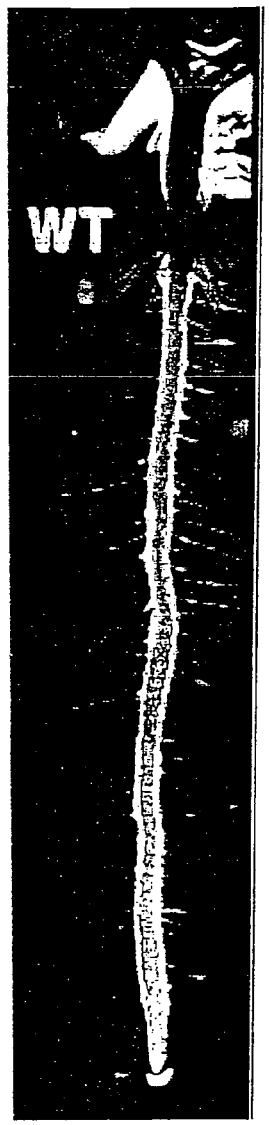
FIGS. 3A, 3B and 3C are photomicrographs of the root and root hairs of representative five day old seedlings obtained from representative WT, AVP1-1 and AVP1-2 plants grown parallel to the surface on vertical plant nutrient agar plates.
Figure 3B:
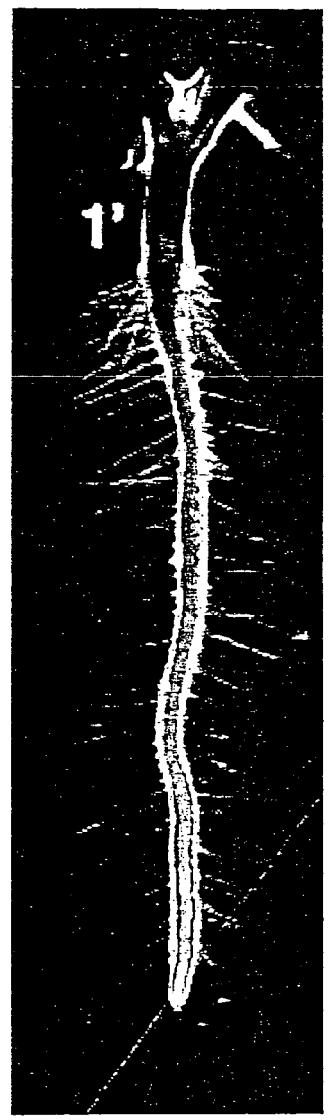
Figure 3C:
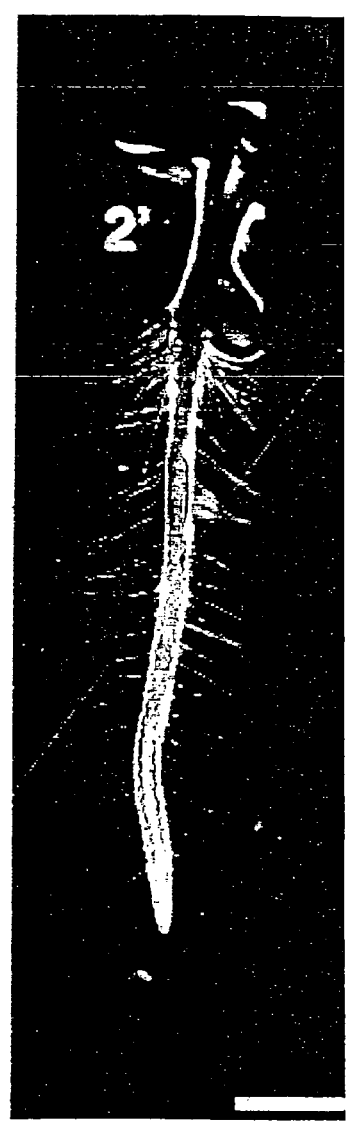

FIG. 3A, FIG. 3B and FIG. 3C are photomicrographs (magnification: times 40; bar length on photograph=2 mm) of the root and root hairs of representative five day old seedlings obtained from representative WT, AVP1-1 transgenic and AVP1-2 transgenic of FIG. 3A grown parallel to the surface on vertical plant nutrient agar plates. Seedlings of both transgenic lines AVP1-1 and AVP1-2 showed root hairs with an average length 40 and 70% larger than wild-type (WT) root hairs (Root hair length along the whole root was determined from five members of each set of seedlings. An average of 80 root hairs per plant were measured). The length of the root hairs is correlated with the size of the vacuole, so the increased size of the root hair is likely to result from increased vacuolar volume. This compares with the *Arabidopsis* mutant rdh3 which has been reported to have reduced vacuolar volume and is a short plant with abnormally short root hairs (M. E. Galway, J. W. J. Heckman, J. W. Schiefelbein, *Planta* 201, 209-218 (1997)). A well characterized mode of plant cell expansion is tip growth, whereby new cell growth is limited to a single growing point and leads to the formation of a tubular-shaped cell. *Plant Physiol.* 103: 979-985 (1993). Two cell tips that are known to display this pattern of tip growth are pollen tubes and root hairs. For root hairs, it is expected that the increased root structure will have a positive impact on soil erosion, nitrogen fixation in legumes, and will aid in water and nutrient uptake by the plant.

Figure 4:
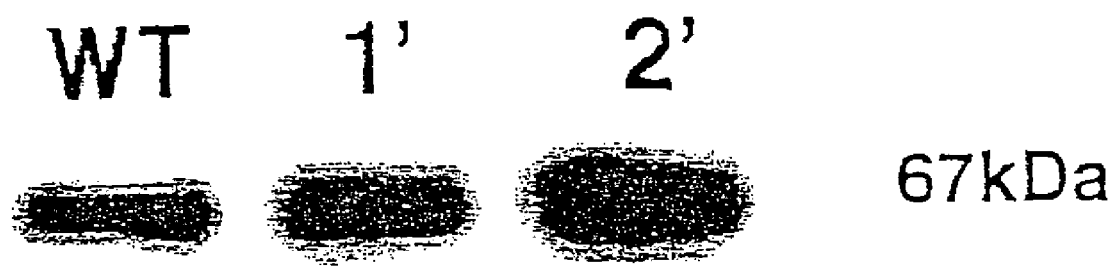
FIG. 4 is an immunoblot of membrane fractions isolated from wild type (WT) and two independent transgenic lines (AVP1-1 and AVP1-2) overexpressing AVP-1.

FIG. 4 is an immunoblot of membrane fractions isolated from wild type (WT) and two independent transgenic lines (AVP1-1 and AVP1-2) overexpressing AVP1. Total membrane fractions were isolated from shoots of eight week old wild type (WT) and AVP-1 transgenic plants (AVP1-1 and AVP1-2) grown in a hydroponic media for 6 weeks. Shoots of plants homogenates were sequentially centrifuged for 15 and 30 min at 8 and 100 kg respectively. The 100 kg membrane pellet was re-suspend in 10 mM Tris, pH 7.5, 150 mM NaCl, 1 mM EDTA, 10% glycerol and 1 mM PMSF Protein (10 mg) was separated on a 10% SDS-PAGE, electroblotted and immunostained with antibodies raised against a KLH-conjugated synthetic peptide corresponding to the putative hydrophilic loop IV of the AVP-1 protein (V. Sarafian, Y. Kim, R. J. Poole, P. A. Rea, *Proc. Natl. Acad. Sci.* 89, 1775-1779 (1992)). PPase was detected by chemiluminescence. FIG. 4 illustrates that the transgenic lines (1' and 2') express AVP-1 protein at higher levels than the wild type (WT).

As wheat that has been deprived of water is rendered more drought tolerant by an increase in cell $K^+$ content (from 100 mM to 300 mM) (S. Gupta, G. Berkowitz, P. Pier, *Plant Physiol* 89, 1358-1365 (1989)), it is hypothesized (but the invention is not hereby limited by such theory) that the increased drought resistance of the AVP-1 transgenic plants may be a consequence of their higher vacuolar concentration of potassium that results in a increased water retention capability. Laboratory tests appear to confirm this.

Figure 5:
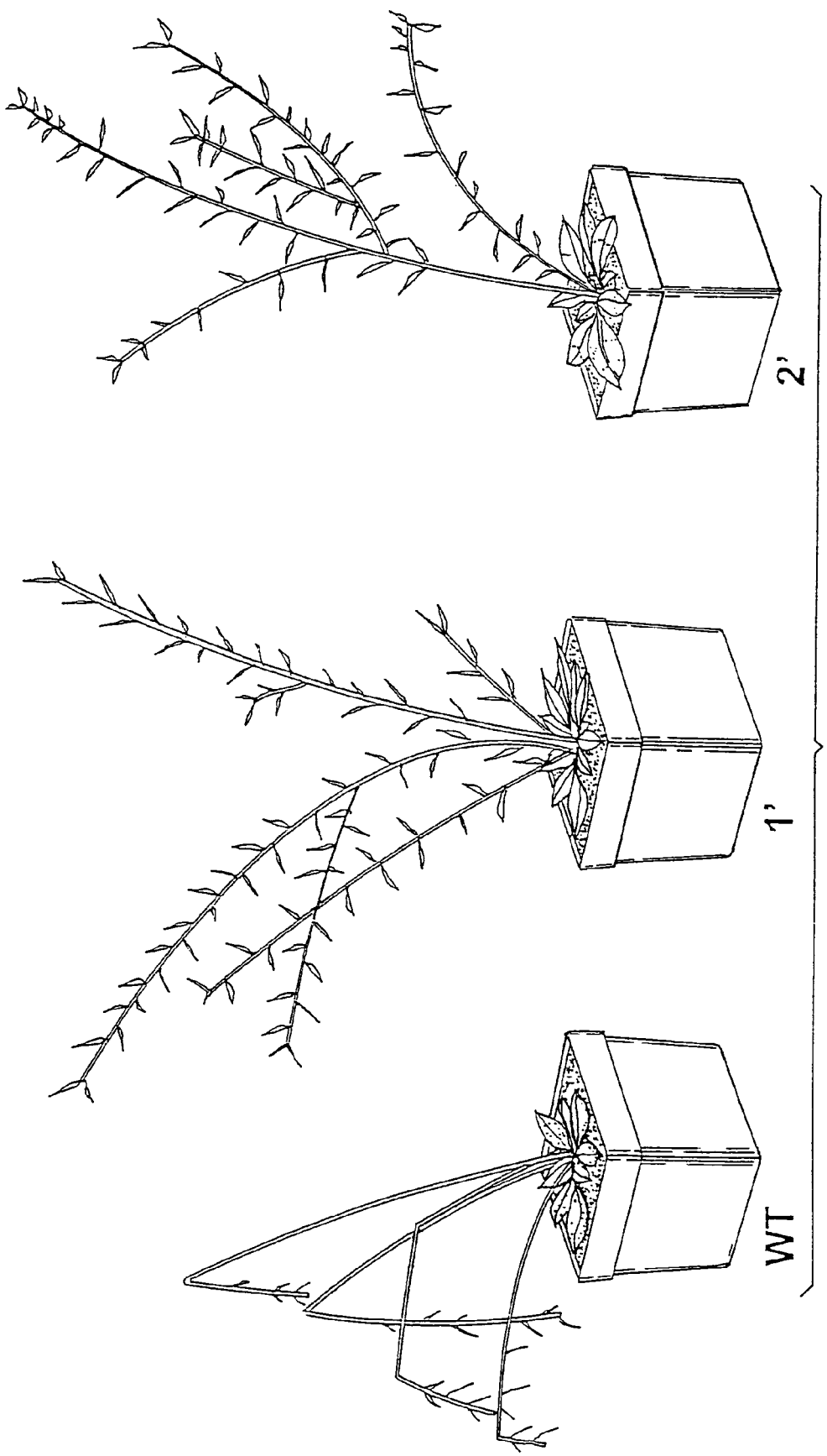
FIG. 5 is a perspective view of wild-type plants (Wt) versus representative transgenic plants overexpressing AVP-1 (AVP1-1 and AVP1-2) grown in salty soil.

FIG. 5 is a perspective view of wild type plants (WT) versus representative transgenic plants overexpressing AVP1 (AVP1-1 and AVP1-2) grown in salty soil. Five wild-type plants (WT) and two AVP-1 overexpressing transgenic lines (AVP1-1 and AVP1-2) were grown on soil in a 10 hour light/dark cycle. Plants were watered with a diluted nutrient solution (1/8 MS salts) for six weeks and subsequently watered with a diluted nutrient solution supplemented with NaCl. The concentration of NaCl began with 100 mM and was increased every four days by 100 mM. The drawing in FIG. 5 corresponds to plants at the tenth day in the presence of 300 mM NaCl. FIG. 5 illustrates that the two AVP-1 plant types (AVP1-1 and AVP1-2) were significantly hardier in salty soil as compared to wild-type plants. The fact that genetically engineered *Arabidopsis thaliana* plants that overexpress either AVP1 (the pyrophosphate-energized vacuolar membrane proton pump, this work) or AtNHX1 (the $Na^+/H^+$ antiporter, (Apse, M., et al., *Science,* 285:1256-1258 (1999)) and this work) are capable of growing in the presence of high NaCl concentrations strongly supports the strategy described herein. A double transgenic plant would be expected to demonstrate a further enhanced salt-tolerant phenotype. These *Arabidopsis thaliana* transporters or their counterparts may perform similar function in important agricultural crops.

A Working Model of Cation Homeostasis in Plant Organelles While the present invention is not limited to any particular hypothesis, the present inventors have developed a working model for cation homeostasis in plant cells which can explain the observed results with respect to the transgenic plants disclosed herein.

In plants, most of the transport processes are energized by the primary translocation of protons. $H^+$-translocating pumps located at the plasma membrane and tonoplast translocated $H^+$ from the cytosol to extracellular and vacuolar compartments, respectively (Rea, P. A., et al., Tonoplast Adenosine Triphosphate and inorganic Pyrophosphatase. In: *Methods Plant Biochem.,* pp. 385-405, Academic Press Limited, London (1990)). The plant tonoplast contains two $H^+$-translocating pumps; the V-ATPase and the inorganic pyrophosphatase or V-PPase. Their action results in luminal acidification and the establishment of a $H^+$ electrochemical potential gradient across the tonoplast (Davies, J. M., et al., The Bioenergetics of Vacuolar $H^+$ Pumps. In: *Plant Vacuole*, pp. 340-363, Leigh, R. A., Sanders, D. (eds.), Academic Press, San Diego (1997)). The vacuolar membrane is implicated in a broad spectrum of physiological processes that include cytosolic pH stasis, compartmentation of regulatory $Ca^{2+}$, sequestration of toxic ions such as $Na^+$, turgor regulation, and nutrient storage and retrieval. The vacuole constitute 40 to 99% of the total intracellular volume of a mature plant cell. The vacuolar proton pumping pyrophosphatase is a universal and abundant component of plant tonoplast capable of generating a steady-state trans-tonoplast $H^+$ electrochemical potential similar or greater than the one generated by the V-ATPase (Rea, P. A., et al., Tonoplast Adenosine Triphosphate and Inorganic Pyrophosphatase. in: *Methods Plant Biochem.*, pp. 385-405, Academic Press Limited, London (1990)). Pyrophosphate (PPi) is a by-product in the activation or polymerization steps of a wide range of biosynthetic pathways and in plants serves as an alternative energy donor to ATP for sucrose mobilization via sucrose synthetase, for glycolysis via PPi: fructose-6-phosphate phosphotransferase and for tonoplast energization via the vacuolar proton pumping pyrophosphatase (Stitt, M., *Bot. Acta* 111:167-175 (1998)).

Most of intracellular organelles, including clathrin-coated vesicles, endosomes, Golgi membranes and vacuoles have acidic interiors (Xie, X. S., et al., *J. Biol. Chem.*, 264:18870-18873 (1989)). This acidification is mediated by a proton-translocating electrogenic ATPase and in plant vacuoles also via a pyrophosphate-driven proton pump V-PPase (Davies, J. M., et al., The Bioenergetics of Vacuolar $H^+$ Pumps. In: Leigh R. A., Sanders, D., (eds) *The Plant Vacuole*, pp. 340-363, Academic Press, San Diego (1997); Zhen, R. G., et al., "The Molecular and Biochemical Basis of Pyrophosphate-Energized Proton Translocation at the Vacuolar Membrane Academic Press Limited (1997)). There exists a requirement of anion transport to maintain net electroneutrality (al-Awqati, A., *Curr. Opin. Cell. Biol.*, 7:504-508 (1995)).

Two transgenic lines of *Arabidopsis thaliana* were analyzed, AVP1-1 and AVP1-2. Each line contains extra copies of the 35S::AVP1 gene inserted at a single chromosomal location. Analysis of AVP1 protein levels in membrane fractions isolated from shoots show that these transgenic plants express more AVP1 protein than does the wild type (AVP1-1, 1.6 fold and AVP1-2, 2.4 fold increase over wild type, P-value=0.0005) (FIG. 4) as determined from four independent Western blots. The differences between these transgenic plants could be due to the number of copies of AVP1 inserted into the genome or the sites of insertion. The transgenic plants overexpressing AVP1 are more salt tolerant than wild type plants (FIG. 5). Plants from both AVP1-1 and AVP1-2 transgenic lines grow well in the presence of up to 250 mM NaCl whereas wild type plants grow poorly and exhibit chlorosis. After 10 days in these conditions wild type plants die, whereas the transgenic plants continue to grow well.

The enhanced tolerance to salinity and drought in transgenic plants with increased levels of AVP1 is most easily explained by an enhanced uptake of toxic cations such as sodium into the vacuole. Presumably, the greater AVP1 activity provides increased $H^+$ to drive the secondary active uptake of cations into the lumen of the vacuole. If so, there must be a compensatory transport of anions to maintain electroneutrality. The resulting elevated vacuolar solute content would confer greater water retention, permitting plants to survive under conditions of low soil water potentials. Furthermore, at high $Na^+$ concentrations, the increased $H^+$ gradient could also enhance the driving force for AtNHX-1-mediated $Na^+/H^+$ exchange, thereby contributing to the $Na^+$ sequestration into the vacuole of AVP1 transgenic plants. Presumably, any toxic effects intrinsic to $Na^+$ are mitigated by this sequestration in the vacuole. This scenario predicts that a transgenic plant engineered to overexpress both, the AVP1 $H^+$-pump and the AtNHX1 $Na^+/H^+$ antiporter would tolerate even higher NaCl stresses than AVP1 and AtNHX1 single transgenic plants.

Figure 6:
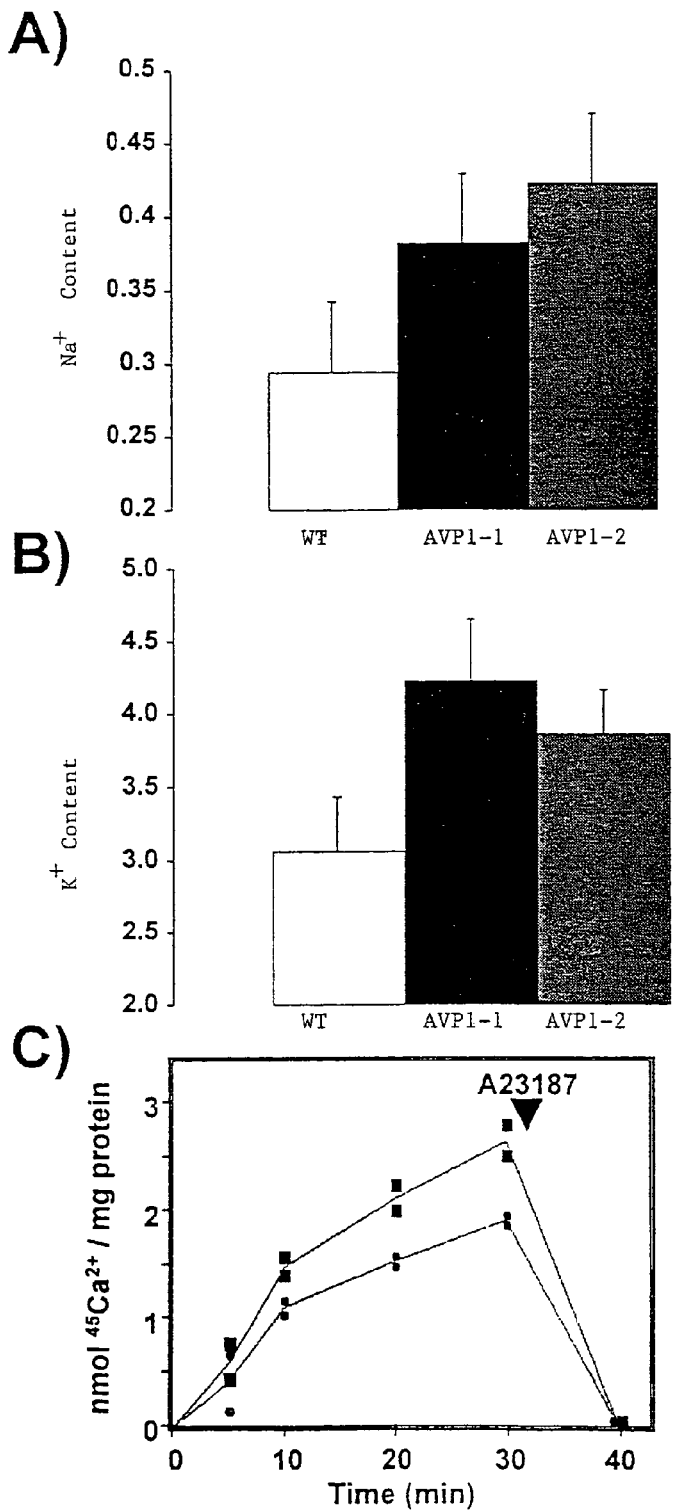
FIG. 6A is a graph showing accumulation of sodium ion in leaf tissue for wild-type plants (WT) versus representative transgenic plants overexpressing AVP-1 (AVP1-1 and AVP1-2).
FIG. 6B is a graph showing accumulation of potassium ion in leaf tissue for wild-type plants (WT) versus representative transgenic plants overexpressing AVP-1 (AVP1-1 and AVP1-2).
FIG. 6C is a graph showing the results of measurements of transport using vacuolar membrane vesicles derived from the AVP1 transgenic plant demonstrating that vacuoles from these plants have enhanced cation uptake capability.

FIGS. 6A and 6B are graphs of $Na^+$ and $K^+$ content of wild-type plants (WT) versus representative transgenic plants overexpressing AVP-1 (1' and 2') grown in salty soil. Five wild-type plants (WT) and two AVP-1 overexpressing transgenic lines (1' and 2') were grown on soil in a 10 hour light/dark cycle. Plants were watered with a diluted nutrient solution (1/8 MS salts) for six weeks and subsequently watered with a diluted nutrient solution supplemented with NaCl. The concentration of NaCl began with 100 mM and was increased every four days by 100 mM. The graphs correspond to plants at the tenth day in the presence of 300 mM NaCl. Parts of the plant above ground were harvested after 24 hours in the presence of 200 mM NaCl and their fresh weigh measured. After 48 hours at 75° C., the dry weight was measured. $Na^+$ and $K^+$ content was determined by atomic absorption. Values in the graphs of FIGS. 6A and 6B are the mean+/−SE (n=4). As can be seen from the graphs $Na^+$ and $K^+$ content in the transgenic lines (1' and 2') was significantly higher than that of wild-type counterparts.

Figure 7:
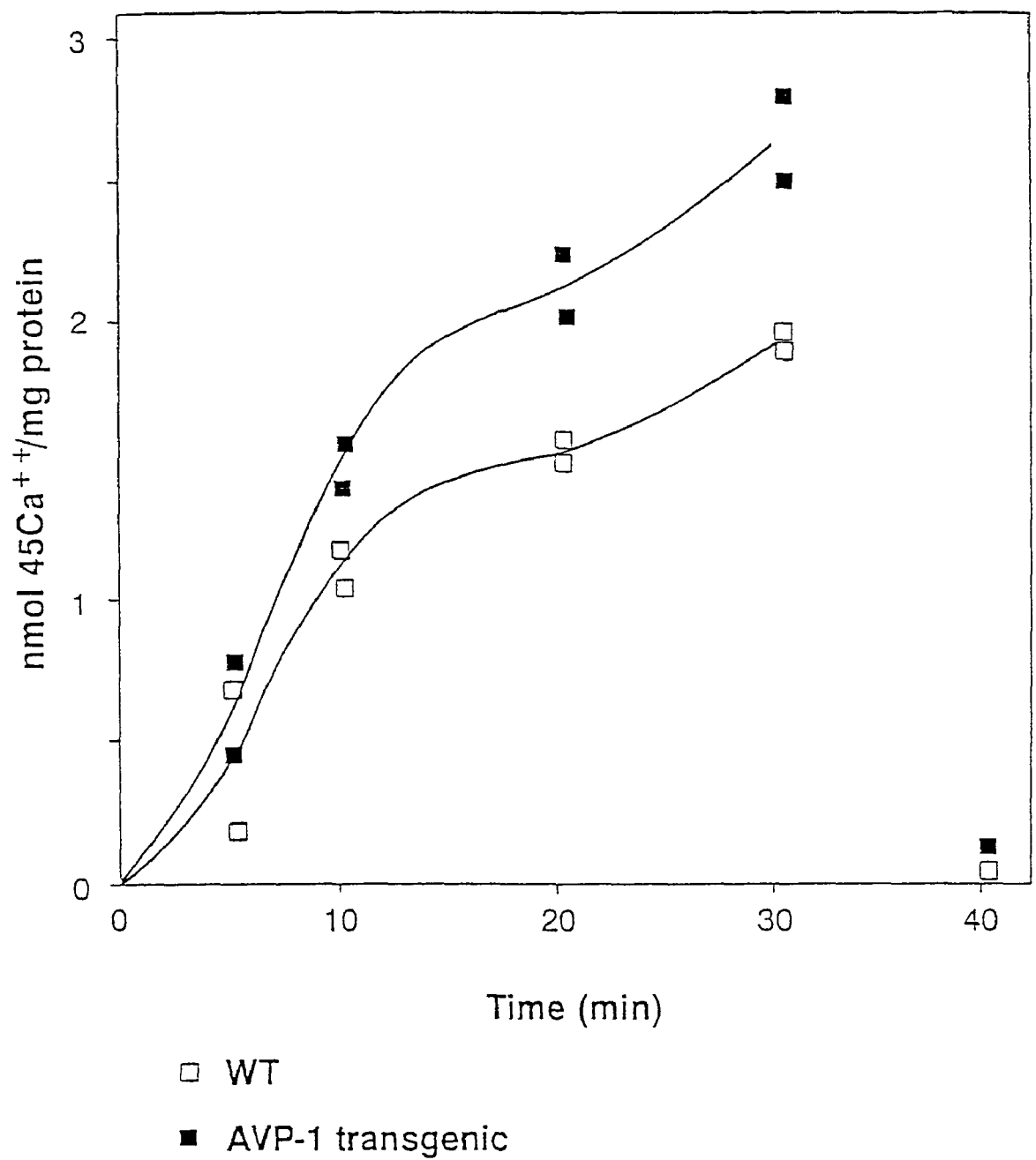
FIG. 7 is a graph of the uptake of calcium into the 35SAVP-1 transgenic vacuolar membrane vesicles (squares) of AVP1-2 FIG. 5 versus calcium uptake into vesicles obtained from wild type (WT) of FIG. 5.

FIG. 7 is a graph of the uptake of calcium into the 35SAVP-1 transgenic vacuolar membrane vesicles (squares) of AVP1-2 versus calcium uptake into vesicles obtained from wild type (WT). Wild-type plants (open circles) and transgenic plants from line AVP1-2 were grown hydroponically for nine weeks on a 10 hour light cycle. Vacuolar membrane vesicles were added to buffer containing 250 mM sorbitol, 25 mM BTP-Hepes pH 8.0, 50 mM KCl, 1.5 nM $MgSO_4$ and 10 μM $Ca^{++}$. This mix was incubated at 20° C. for 10 minutes before adding 200 μM PPi to trigger the reaction. $Ca^{++}$ ionophore A23187 was added to a final concentration of 5 μg/ml to dissipate the $Ca^{++}$ gradient. Aliquot (200 μl) were filtered at the indicated times and washed with cold buffer as described (11). As is evidenced by the graphs, the transgenic plants from line 2' have greater calcium uptake than wild-type plants.

The above data is consistent with the hypothesis that transgenic plants overexpressing AVP-1 have an enhanced $H^+$ pumping capability at their tonoplast and that an enhanced $H^+$ supply results in greater ion accumulation in the vacuole through the action of $H^+$-driven ion transporters. To further support this theory, $Ca^{++}$ uptake capability of wild type and transgenic vacuolar membrane vesicles was determined.

It is well documented that $Ca^{++}$ enters the plant vacuole via a $Ca^{++}/H^+$ antiporter (K. S. Schumaker, H. Sze, *Plant Physiol.* 79, 1111-1117 (1985)). Furthermore, the genes encoding the *Arabidopsis thaliana* $Ca^{++}/H^+$ antiporters CAX1 and CAX2 have been isolated and characterized (K. D. Hirschi, R.-G. Zhen, K. W. Cunningham, P. A. Rea, G. R. Fink, *Proc. Natl. Acad. Sci. USA* 93, 8782-8786 (1996)). FIG. 7 shows that $Ca^{++}$ uptake in the 35SAVP-1 transgenic vacuolar membrane vesicles is 36% higher than it is in vesicles obtained from wild type. Application of the $Ca^{++}$ ionophore A23 lowered the $45Ca^{++}$ counts to background levels demonstrating the tightness of the vesicles (FIG. 7) (K. S. Schumaker, H. Sze, *Plant Physiol.* 79, 1111-1117 (1985)).

While not limited by such theory, a model consistent with the enhanced drought and freeze tolerance of the transgenic plants overexpressing the AVP-1 gene is depicted in FIGS. 8A and 8B. The model depicts how an increase in the number of AVP-1 pumps in the vacuole of transgenic plants can provide more $H^+$ that will permit the secondary transporters to import greater amounts of cations into the lumen of the vacuoles. Higher amounts of cations confer a greater osmotic pressure that leads to a greater water retention capability endowing plants to withstand low soil water potentials.

The present invention relates, in one aspect, to pollen produced by a transgenic plant transformed with a tonoplast pyrophosphatase driven H+ pump gene operably linked to a promoter. In a second aspect, the invention relates to methods for increasing the production of seeds in plants using pollen from a transgenic plant transformed with a tonoplast pyrophosphatase driven H+ pump gene operably linked to a promoter.

Transgenic plants that overexpress a vacuolar proton-pumping pyrophosphatase such as, for example, AVP 1, also produce an increased yield of seeds. Referring to FIG. 1, the seed yield, as expressed by the weight of seeds produced, is higher for AVP1-1 transgenic plants as compared to wild type plants. This increased seed yield is a result of the pollen from the transgenic plant having an enhanced ability to fertilize, referred to herein as fertilization competence.

To demonstrate that the improved seed yield is a result of the improved fertilization competence of the pollen from the transgenic plant, the pollen from wild type Arabidosis thaliana plants was used for pollination of two lines of transgenic Arabidosis thaliana plants transformed to overexpress AVP 1 (these two lines of transgenic plants are referred to herein as AVP 1-1 and AVP 1-2). Referring to FIGS. 10A and 10B, the transgenic plants pollinated with pollen from wild type plants produced an average of between about 15 and 20 seeds, with an average seed pod mass of between about 2.5 and 3 milligrams. These results were compared to the seed yield obtained when pollen from the two lines of Arabidosis thaliana transgenic plants was used to pollinate wild type Arabidosis thaliana plants. Referring again to FIGS. 10A and 10B, the wild type plants fertilized with transgenic pollen produced an average of between about 30 and 35 seeds, with an average seed pod mass of between about 4 and 5 milligrams.

These results demonstrate that pollen from transgenic plants transformed with a tonoplast pyrophosphatase-driven H$^+$ pump gene is capable of causing improved seed yield in plants fertilized with the transgenic pollen. To further illustrate, wild type plants that are fertilized with transgenic pollen also produce an increased yield of seeds, while transgenic plants fertilized with wild type pollen do not. These results clearly indicate that it is the pollen from the transgenic plant, and not the female reproductive organs of the transformed plant, that causes improved seed yield.

Similar results have also been observed in other plant species transformed to overexpress a vacuolar proton-pumping pyrophosphatase Referring to FIG. 11, the volume of seeds produced by wild type tobacco plants is compared to the seed pod volume produced in transgenic tobacco plants transformed to overexpress a vacuolar proton-pumping pyrophosphatase. The volume of five seed pods from each plant was weighed. For the wild type tobacco plants, the volume of seeds in five pods was between about 0.5 milliliters and 0.8 milliliters. For the three lines of transgenic tobacco plants tested, the volume of seeds in five pods was between about 1.2 milliliters and 1.4 milliliters. The transgenic tobacco lines were crossed and the volume of five seed pods was measured. The volume of five seed pods from the crossed lines of tobacco plants remained between about 1.2 milliliters and 1.4 milliliters.

These results further demonstrate that it is the pollen from the transgenic plants that improve seed yield. All three lines of transgenic tobacco plants had substantially greater seed pod volume than wild type plants. In addition, when the three lines of transgenic tobacco plants were crossed, the seed pod volume was about the same as the seed pod volume of the uncrossed transgenic line, and much greater than the seed pod volume from the wild type line.

Most food plants of interest are hermaphroditic and will self-pollinate. Transgenic plants of this type that have been transformed to overexpress a vacuolar proton-pumping pyrophosphatase will themselves produce increased seed yields as a result of the improved fertilization competence of their pollen.

In another aspect of the present invention, which is especially useful for plant species which do not self-pollinate, pollen is provided from a transgenic plant transformed with a tonoplast pyrophosphatase driven H+ pump gene operably linked to a promoter. The pollen from the transgenic plant is used to fertilize transgenic or wild type female flowers. Fertilization of the wild type plant is accomplished using any appropriate method known to one skilled in the art.

After the wild type plant has been fertilized, the plant is cultured until the wild type plant produces mature seeds. The mature seeds are harvested from the wild type plant after they reach maturity. This increase in seed yield is a result of the improved competence of the pollen from the transgenic plant in fertilization.

In another embodiment of the present invention, the pollen from a transgenic plant transformed with a tonoplast pyrophosphatase driven H+ pump gene operably linked to a promoter is used to fertilize a transgenic plant which has also been transformed with a tonoplast pyrophosphatase driven H+ pump gene operably linked to a promoter. After the transgenic plant has been fertilized, the plant is cultured until it produces mature seeds. The mature seeds are harvested from the transgenic plant after they reach maturity.

As will be recognized by those of ordinary skill in the art based on the teachings herein, numerous changes and modifications may be made to the above-described embodiments of the present invention without departing from its scope or spirit. Accordingly, this detailed description of the invention is to be takeri in an illustrative rather than a limiting sense.

What is claimed is:

1. Transgenic pollen containing an exogenous nucleic acid, wherein the exogenous nucleic acid comprises a nucleic acid sequence encoding a plant vacuolar pyrophosphatase operably linked to at least one regulatory element that promotes expression of the plant vacuolar pyrophosphatase in the transgenic pollen.

2. The transgenic pollen of claim 1, wherein the transgenic pollen is obtained from a plant selected from the group consisting of tomato, rice, tobacco, sorghum, cucumber, lettuce, turf grass, *Arabidopsis* and corn.

3. The transgenic pollen of claim 1, wherein the nucleic acid sequence encoding a plant vacuolar pyrophosphatase is from a plant of the same species as the plant that produced the pollen.

4. The transgenic pollen of claim 1, wherein the nucleic acid sequence encoding a plant vacuolar pyrophosphatase is from a plant of a species different from the plant that produced the pollen.

5. The transgenic pollen of claim 1, wherein the nucleic acid sequence encoding a plant vacuolar pyrophosphatase is obtained from a plant selected from the group consisting of *Arabidopsis*, tobacco, tomato and corn.

6. The transgenic pollen of claim 1, wherein the plant vacuolar pyrophosphatase is AVP1 or a homolog thereof and wherein said homolog has plant vacuolar pyrophosphatase activity.

7. A seed-producing plant fertilized with transgenic pollen of claim 1, said seed producing plant producing seeds higher in yield compared to the yield of seeds produced by plants of the same species fertilized with wild-type pollen.

8. The seed-producing plant of claim 7, wherein the seed-producing plant is selected from the group consisting of tomato, rice, tobacco, sorghum, cucumber, lettuce, turf grass, *Arabidopsis* and corn.

9. The seed-producing plant of claim 7, wherein the nucleic acid sequence encoding a plant vacuolar pyrophosphatase is from the seed-producing plant.

10. The seed-producing plant of claim 7, wherein the nucleic acid sequence encoding a plant vacuolar pyrophosphatase is from a non-transgenic wild-type plant of a species different from the seed-producing plant.

11. The seed-producing plant of claim 7, wherein the nucleic acid sequence encoding a plant vacuolar pyrophosphatase is obtained from a plant selected from the group consisting of *Arabidopsis*, tobacco, tomato and corn.

12. The seed-producing plant of claim 7, wherein the plant vacuolar pyrophosphatase is AVP1 or a homolog thereof and wherein said homolog has plant vacuolar pyrophosphatase activity.

13. Transgenic progeny of the seed-producing plant of claim 7, wherein the transgenic progeny contains an exogenous nucleic acid comprising a nucleic acid sequence encoding a plant vacuolar pyrophosphatase operably linked to at least one regulatory element that promotes expression of the plant vacuolar pyrophosphatase.

14. Transgenic seeds produced by the transgenic plant of claim 7, wherein the transgenic seeds comprise an exogenous nucleic acid comprising a nucleic acid sequence encoding a plant vacuolar pyrophosphatase operably linked to at least one regulatory element that promotes expression of the plant vacuolar pyrophosphatase.

15. Transgenic progeny grown from the transgenic seeds of claim 14.

16. The seed-producing plant of claim 7, wherein the seed-producing plant is a hermaphroditic transgenic plant that produces self-pollinating transgenic pollen having improved fertilization competence, and wherein the hermaphroditic transgenic plant comprises said exogenous nucleic acid and has increased seed production relative to non-transgenic wild-type plants of the same species.

17. A seed-producing transgenic plant, said transgenic plant containing one or more transgenic plant cells comprising an exogenous nucleic acid that causes overexpression of a plant vacuolar pyrophosphatase in the one or more transgenic plant cells, wherein said seed-producing transgenic plant produces pollen having improved fertilization competence relative to pollen from non-transgenic wild-type plants of the same species.

18. The seed-producing transgenic plant of claim 17, wherein the transgenic plant is selected from the group consisting of tomato, rice, tobacco, sorghum, cucumber, lettuce, turf grass, *Arabidopsis* and corn.

19. The seed-producing transgenic plant of claim 17, wherein the nucleic acid is from a non-transgenic wild-type plant of the same species as the transgenic plant.

20. The seed-producing transgenic plant of claim 17, wherein the nucleic acid is from a non-transgenic wild-type plant of a species different from the transgenic plant.

21. The seed-producing transgenic plant of claim 17, wherein the nucleic acid is obtained from a plant selected from the group consisting of *Arabidopsis*, tobacco, tomato and corn.

22. The seed-producing transgenic plant of claim 17, wherein the nucleic acid comprises a sequence encoding the plant vacuolar pyrophosphatase operably linked to at least one regulatory element that results in overexpression of the plant vacuolar pyrophosphatase.

23. The seed-producing transgenic plant of claim 22, wherein the regulatory element is selected from the group consisting of tissue-specific promoters, constitutive promoters, inducible promoters and promoters that are both tissue-specific and inducible.

24. The seed-producing transgenic plant of claim 22, wherein the nucleic acid sequence encoding the plant vacuolar pyrophosphatase is operably linked to a double tandem enhancer of a 35S CaMV promoter.

25. The seed-producing transgenic plant of claim 17, wherein the plant vacuolar pyrophosphatase is AVP1 or a homolog thereof and wherein said homolog has plant vacuolar pyrophosphatase activity.

26. Transgenic progeny of the seed-producing transgenic plant of claim 17, wherein the transgenic progeny comprise the exogenous nucleic acid of claim 17.

27. Transgenic seeds produced by the seed-producing transgenic plant of claim 17, wherein the transgenic seeds comprise the exogenous nucleic acid of claim 17.

28. Transgenic progeny grown from the transgenic seeds of claim 27.

29. A method for increasing production of seeds in plants, said method comprising:
    (a) providing pollen comprising an exogenous nucleic acid that causes overexpression of a plant vacuolar pyrophosphatase in the pollen;
    (b) fertilizing a plant with the pollen; and
    (c) culturing the fertilized plant until the plant produces mature seeds.

30. The method of claim 29, wherein the plant fertilized with the pollen is a transgenic plant comprising the exogenous nucleic acid that causes overexpression of the plant vacuolar pyrophosphatase.

31. The method of claim 29, wherein the plant fertilized with the pollen is a non-transgenic wild-type plant.

32. The method of claim 29, wherein the plant fertilized with the pollen is selected from the group consisting of *Nicotiana tabacum* and *Arabidopsis thaliana*.

33. The method of claim 29, wherein the nucleic acid sequence encoding the plant vacuolar pyrophosphatase is from the same species as the plant that produces the pollen.

34. The method of claim 29, wherein the nucleic acid sequence encoding the plant vacuolar pyrophosphatase is from a species different from the plant that produces the pollen.

35. The method of claim 29, wherein the nucleic acid sequence encoding the plant vacuolar pyrophosphatase is obtained from a plant selected from the group consisting of *Arabidopsis*, tobacco, tomato and corn.

36. The method of claim 29, wherein the nucleic acid comprises a sequence encoding the plant vacuolar pyrophosphatase operably linked to at least one regulatory element that results in overexpression of the plant vacuolar pyrophosphatase.

37. The method of claim 36, wherein the regulatory element is selected from the group consisting of tissue-specific promoters, constitutive promoters, inducible promoters and promoters that are both tissue-specific and inducible.

38. The method of claim 36, wherein the nucleic acid sequence encoding the plant vacuolar pyrophosphatase is operably linked to a double tandem enhancer of a 35S CaMV promoter.

39. The method of claim 37, wherein the nucleic acid sequence encoding the plant vacuolar pyrophosphatase is operably linked to a promoter that promotes expression of the plant vacuolar pyrophosphatase in pollen.

40. The method of claim 29, wherein the plant vacuolar pyrophosphatase is AVP1 or a homolog thereof and wherein said homolog has plant vacuolar pyrophosphatase activity.

41. Transgenic pollen containing exogenous nucleic acid that produces overexpression of a plant vacuolar pyrophosphatase in the transgenic pollen.

42. A seed-producing transgenic plant fertilized with the transgenic pollen of claim 41.

43. A transgenic progeny of the seed-producing transgenic plant of claim 42 wherein the transgenic progeny comprises said exogenous nucleic acid.

\* \* \* \* \*

SEQUENCE LISTING

```
<160> NUMBER OF SEQ ID NOS: 2

<210> SEQ ID NO 1
<211> LENGTH: 2813
<212> TYPE: DNA
<213> ORGANISM: Arabidopsis thaliana

<400> SEQUENCE: 1
cttagattta tctttgagtc ccgaaacatc gaggaacgcc ttcgaatccc tctctctctg      60
tgtgtgttct ctgtgttctc tctctcgcgc gaagcggttc tctttctttt gtttatttgt     120
ttttatttgt ttttctctta tacggaggag agaagatggt ggcgcctgct ttgttaccgg     180
```

-continued

```
agctctggac ggagatcctt gtaccgattt gtgcggtgat tggtatcgcc ttttcgcttt      240
tccaatggta cgttgtatct cgcgtgaaac tcacctctga cctcggcgca tcgtcttccg      300
gtggagctaa caatgggaag aatggatacg gtgattatct aatcgaggaa gaggaaggtg      360
ttaatgacca gagtgttgtc gctaagtgcg ctgagattca gactgctatt ccgaaggtg      420 caacttcatt cctattcacg gagtacaaat atgttggtgt cttcatgatt ttctttgctg      480
ctgttatctt tgttttcctc ggctctgttg agggattcag cactgataac aagccttgta      540
cttacgacac caccagaacc tgcaagcctg cattggctac tgcagctttc agtaccattg      600
ctttcgtgct tggtgctgtt acctctgttc tatctggttt ccttgggatg aagattgcta      660
catacgctaa tgctaggacc actttggagg cgaggaaagg tgttggaaag gcgttcattg      720
ttgcattcag gtctggtgct gtgatgggtt tccttcttgc agcgagtggt ctattggtgc      780
tttacattac tatcaatgtg ttcaagatct attacggaga tgactgggaa ggtctttttg      840
aggctattac tggttatggt cttggtgggt cttccatggc tctcttggc cgtgttggtg      900 gtgggatcta cactaaggct gctgatgtcg gcgctgacct tgtcggtaaa attgagagga      960
atattccaga ggatgatcca agaaacccag ctgtcattgc tgataatgtc ggtgacaatg     1020
ttggtgacat tgctggtatg ggatctgatc tctttggatc atatgctgaa gcatcatgcg     1080
ctgctcttgt tgttgcctcg atctcatctt tcggaatcaa ccacgacttc actgccatgt     1140
gctacccatt gctcatcagt tcaatgggaa tcttggtttg tttgatcaca actctctttg     1200
ccactgactt ctttgagatt aagcttgtca aggagattga accagcattg aagaaccagc     1260
tcattatctc aactgttatt atgactgttg gtattgctat tgtgtcatgg gttggcttac     1320
cgacctcctt taccatcttc aactttggaa cacaaaaagt tgtcaagaac tggcagctat     1380
tcctttgtgt ttgtgttggt ctttgggctg gactcattat tggtttcgtc actgagtact     1440
acactagtaa cgcctacagc cctgtgcaag atgttgcaga ttcatgcaga actggtgcag     1500
ctaccaatgt tatcttcggc cttgctcttg gttacaaatc cgtcattatt ccaatctttg     1560
ctattgctat cagtatattc gttagcttca gctttgctgc tatgtatggt gttgctgttg     1620
ctgctcttgg tatgctcagt accattgcca ctggtttggc aattgatgct tatggtccca     1680
tcagtgacaa tgctggtggt attgctgaaa tggctggaat gagccaccgc atccgtgaaa     1740
gaactgatgc tcttgatgcc gctggaaaca ccactgctgc tattggaaag ggatttgcca     1800
ttggctctgc tgccctagtc tccttggctc tctttggtgc ctttgtgagc cgtgcaggga     1860
tccacaccgt agatgttttg accccctaaag ttatcattgg gctccttgtt ggtgccatgc     1920
ttccttactg gttctctgcc atgacaatga gagtgtggg aagtgcagct cttaagatgg     1980
ttgaagaagt tcgcaggcag ttcaacacca tccctggact tatggaagga accgcaaaac     2040
cagactacgc cacatgtgtc aagatctcca ccgatgcttc catcaaggaa atgatacctc     2100
ctggttgcct tgtcatgctc acacctctca ttgttggttt cttctttgga ttgagaccc      2160 tctctggtgt cctcgccgga tctcttgtat ccggtgttca gatcgccata tcagcatcta     2220
acactggtgg tgcctgggac aacgccaaga aatacatcga ggctggtgta tcagagcacg     2280
caaagagcct tggaccaaag ggttcagagc cacacaaggc agctgtgatt ggagacacaa     2340
ttggagaccc attgaaggat acttcaggac cttcattgaa catcctcatc aagctcatgg     2400
ctgttgagtc tcttgtcttt gctcccttct tcgccactca cggtggtatc cttttcaagt     2460
acttctaaac tcaatccgag ggaagaagat gacgatgatg aagaagaaga agatgatgat     2520
ggcgatcgat tctaaacttt cttttttacc attcttattt tcgtttaccg taggtggtta     2580
```

-continued

```
aaaaacctttt tgttgatga ggctcattta agaaccaac caaatgatgt ttctttctct      2640
cactctctgt ctttctgttt ctttttgtt ctgtttagaa tttagaaatc caccaagtat      2700
tcggtcgaga cttgttttag ccgttacttt ctgctgctta tatttcctaa attggttgtc    2760
ttcttcgaaa cataattgga atttattgtt actgttagtc taaaaaaaaa aaa            2813

<210> SEQ ID NO 2
<211> LENGTH: 770
<212> TYPE: PRT
<213> ORGANISM: Arabidopsis thaliana

<400> SEQUENCE: 2

Met Val Ala Pro Ala Leu Leu Pro Glu Leu Trp Thr Glu Ile Leu Val
1               5                   10                  15

Pro Ile Cys Ala Val Ile Gly Ile Ala Phe Ser Leu Phe Gln Trp Tyr
                20                  25                  30

Val Val Ser Arg Val Lys Leu Thr Ser Asp Leu Gly Ala Ser Ser Ser
            35                  40                  45

Gly Gly Ala Asn Asn Gly Lys Asn Gly Tyr Gly Asp Tyr Leu Ile Glu
        50                  55                  60

Glu Glu Glu Gly Val Asn Asp Gln Ser Val Val Ala Lys Cys Ala Glu
65                  70                  75                  80

Ile Gln Thr Ala Ile Ser Glu Gly Ala Thr Ser Phe Leu Phe Thr Glu
                85                  90                  95

Tyr Lys Tyr Val Gly Val Phe Met Ile Phe Phe Ala Ala Val Ile Phe
                100                 105                 110

Val Phe Leu Gly Ser Val Glu Gly Phe Ser Thr Asp Asn Lys Pro Cys
            115                 120                 125

Thr Tyr Asp Thr Thr Arg Thr Cys Lys Pro Ala Leu Ala Thr Ala Ala
        130                 135                 140

Phe Ser Thr Ile Ala Phe Val Leu Gly Ala Val Thr Ser Val Leu Ser
145                 150                 155                 160

Gly Phe Leu Gly Met Lys Ile Ala Thr Tyr Ala Asn Ala Arg Thr Thr
                165                 170                 175

Leu Glu Ala Arg Lys Gly Val Gly Lys Ala Phe Ile Val Ala Phe Arg
                180                 185                 190

Ser Gly Ala Val Met Gly Phe Leu Leu Ala Ala Ser Gly Leu Leu Val
            195                 200                 205

Leu Tyr Ile Thr Ile Asn Val Phe Lys Ile Tyr Tyr Gly Asp Asp Trp
        210                 215                 220

Glu Gly Leu Phe Glu Ala Ile Thr Gly Tyr Gly Leu Gly Gly Ser Ser
225                 230                 235                 240

Met Ala Leu Phe Gly Arg Val Gly Gly Gly Ile Tyr Thr Lys Ala Ala
                245                 250                 255

Asp Val Gly Ala Asp Leu Val Gly Lys Ile Glu Arg Asn Ile Pro Glu
            260                 265                 270

Asp Asp Pro Arg Asn Pro Ala Val Ile Ala Asp Asn Val Gly Asp Asn
        275                 280                 285

Val Gly Asp Ile Ala Gly Met Gly Ser Asp Leu Phe Gly Ser Tyr Ala
    290                 295                 300

Glu Ala Ser Cys Ala Ala Leu Val Val Ala Ser Ile Ser Ser Phe Gly
305                 310                 315                 320

Ile Asn His Asp Phe Thr Ala Met Cys Tyr Pro Leu Leu Ile Ser Ser
                325                 330                 335

Met Gly Ile Leu Val Cys Leu Ile Thr Thr Leu Phe Ala Thr Asp Phe
```

-continued

```
                340             345             350
Phe Glu Ile Lys Leu Val Lys Glu Ile Glu Pro Ala Leu Lys Asn Gln
            355                 360                 365
Leu Ile Ile Ser Thr Val Ile Met Thr Val Gly Ile Ala Ile Val Ser
            370                 375                 380
Trp Val Gly Leu Pro Thr Ser Phe Thr Ile Phe Asn Phe Gly Thr Gln
385                 390                 395                 400
Lys Val Val Lys Asn Trp Gln Leu Phe Leu Cys Val Cys Val Gly Leu
                405                 410                 415
Trp Ala Gly Leu Ile Ile Gly Phe Val Thr Glu Tyr Tyr Thr Ser Asn
                420                 425                 430
Ala Tyr Ser Pro Val Gln Asp Val Ala Asp Ser Cys Arg Thr Gly Ala
            435                 440                 445
Ala Thr Asn Val Ile Phe Gly Leu Ala Leu Gly Tyr Lys Ser Val Ile
            450                 455                 460
Ile Pro Ile Phe Ala Ile Ala Ile Ser Ile Phe Val Ser Phe Ser Phe
465                 470                 475                 480
Ala Ala Met Tyr Gly Val Ala Val Ala Ala Leu Gly Met Leu Ser Thr
                485                 490                 495
Ile Ala Thr Gly Leu Ala Ile Asp Ala Tyr Gly Pro Ile Ser Asp Asn
            500                 505                 510
Ala Gly Gly Ile Ala Glu Met Ala Gly Met Ser His Arg Ile Arg Glu
            515                 520                 525
Arg Thr Asp Ala Leu Asp Ala Ala Gly Asn Thr Thr Ala Ala Ile Gly
            530                 535                 540
Lys Gly Phe Ala Ile Gly Ser Ala Ala Leu Val Ser Leu Ala Leu Phe
545                 550                 555                 560
Gly Ala Phe Val Ser Arg Ala Gly Ile His Thr Val Asp Val Leu Thr
                565                 570                 575
Pro Lys Val Ile Ile Gly Leu Leu Val Gly Ala Met Leu Pro Tyr Trp
            580                 585                 590
Phe Ser Ala Met Thr Met Lys Ser Val Gly Ser Ala Ala Leu Lys Met
            595                 600                 605
Val Glu Glu Val Arg Arg Gln Phe Asn Thr Ile Pro Gly Leu Met Glu
            610                 615                 620
Gly Thr Ala Lys Pro Asp Tyr Ala Thr Cys Val Lys Ile Ser Thr Asp
625                 630                 635                 640
Ala Ser Ile Lys Glu Met Ile Pro Pro Gly Cys Leu Val Met Leu Thr
                645                 650                 655
Pro Leu Ile Val Gly Phe Phe Phe Gly Val Glu Thr Leu Ser Gly Val
            660                 665                 670
Leu Ala Gly Ser Leu Val Ser Gly Val Gln Ile Ala Ile Ser Ala Ser
            675                 680                 685
Asn Thr Gly Gly Ala Trp Asp Asn Ala Lys Lys Tyr Ile Glu Ala Gly
            690                 695                 700
Val Ser Glu His Ala Lys Ser Leu Gly Pro Lys Gly Ser Glu Pro His
705                 710                 715                 720
Lys Ala Ala Val Ile Gly Asp Thr Ile Gly Asp Pro Leu Lys Asp Thr
                725                 730                 735
Ser Gly Pro Ser Leu Asn Ile Leu Ile Lys Leu Met Ala Val Glu Ser
            740                 745                 750
```

```
Leu Val Phe Ala Pro Phe Phe Ala Thr His Gly Gly Ile Leu Phe Lys
        755                 760                 765
Tyr Phe
    770
```